United States Patent
Gwon

(10) Patent No.: US 12,415,112 B2
(45) Date of Patent: Sep. 16, 2025

(54) PORTABLE BREATHING MEASUREMENT AND BREATHING EXERCISE DEVICE

(71) Applicant: GHINNOTEK CO., LTD., Busan (KR)

(72) Inventor: Yu Hong Gwon, Busan (KR)

(73) Assignee: GHINNOTEK CO., LTD., Busan (KR)

( * ) Notice: Subject to any disclaimer, the term of this patent is extended or adjusted under 35 U.S.C. 154(b) by 43 days.

(21) Appl. No.: 18/564,402

(22) PCT Filed: Oct. 28, 2021

(86) PCT No.: PCT/KR2021/015324
§ 371 (c)(1),
(2) Date: Nov. 27, 2023

(87) PCT Pub. No.: WO2023/003088
PCT Pub. Date: Jan. 26, 2023

(65) Prior Publication Data
US 2024/0245953 A1    Jul. 25, 2024

(30) Foreign Application Priority Data

Jul. 23, 2021 (KR) .......................... 10-2021-0096821

(51) Int. Cl.
*A63B 23/18* (2006.01)
*A63B 21/00* (2006.01)
(Continued)

(52) U.S. Cl.
CPC ........ *A63B 23/18* (2013.01); *A63B 21/00069* (2013.01); *A63B 24/0062* (2013.01);
(Continued)

(58) Field of Classification Search
CPC .............. A63B 23/18; A63B 21/00069; A63B 24/0062; A63B 24/0075; A63B 71/0622;
(Continued)

(56) References Cited

U.S. PATENT DOCUMENTS

| 3,674,910 A | * | 7/1972 | McKenzie | ............... G10D 7/14 |
| | | | | 984/137 |
| 4,196,650 A | * | 4/1980 | Fricke | .................. G10H 1/0558 |
| | | | | 84/718 |

(Continued)

FOREIGN PATENT DOCUMENTS

| JP | 2012-187292 A | 10/2012 |
| JP | 2015-093039 A | 5/2015 |

(Continued)

OTHER PUBLICATIONS

International Search Report for PCT/KR2021/015324 mailed Apr. 19, 2022 from Korean Intellectual Property Office.
(Continued)

*Primary Examiner* — Garrett K Atkinson
(74) *Attorney, Agent, or Firm* — Paratus Law Group, PLLC

(57) ABSTRACT

A portable breathing measurement and breathing exercise device includes a body part; a mouthpiece part coupled to one side of the body part; a sensor unit which is provided inside the body part and measures the pressure of a user's breathing via the mouthpiece part; a control unit which receives measurement values from the sensor part and stores the measurement values in real time, analyzes the user's breathing on the basis of the measurement values, and provides an exercise schedule; and a display unit for outputting the analysis results and exercise schedule of the control unit. The mouthpiece part includes a load adjustment unit for regulating the flow rate of air that flows in and out of the mouthpiece part and the body part due to the user's breathing.

4 Claims, 23 Drawing Sheets

(51) Int. Cl.
  *A63B 24/00*  (2006.01)
  *A63B 71/06*  (2006.01)
(52) U.S. Cl.
  CPC ...... *A63B 24/0075* (2013.01); *A63B 71/0622* (2013.01); *A63B 2071/0658* (2013.01); *A63B 2220/56* (2013.01); *A63B 2225/20* (2013.01)
(58) Field of Classification Search
  CPC ........ A63B 2071/0658; A63B 2220/56; A63B 2225/20; A63B 2024/0093; A63B 2230/405; A63B 21/0085; A63B 23/185; A63B 2225/50; A63B 24/0087; A61B 5/00; A61B 5/087; A61B 5/091; G16H 20/30
  See application file for complete search history.

(56)  References Cited

U.S. PATENT DOCUMENTS

| | | | | |
|---|---|---|---|---|
| 5,042,467 | A * | 8/1991 | Foley | A61M 15/0086 128/200.14 |
| 5,899,832 | A * | 5/1999 | Hougen | A63B 23/18 482/13 |
| 6,058,932 | A * | 5/2000 | Hughes | A61M 16/0006 482/13 |
| 6,083,141 | A * | 7/2000 | Hougen | A61M 16/0006 128/202.16 |
| 6,176,235 | B1 * | 1/2001 | Benarrouch | A61M 16/20 128/205.12 |
| 6,326,532 | B1 * | 12/2001 | Antaki | G10D 7/14 84/377 |
| 6,702,769 | B1 * | 3/2004 | Fowler-Hawkins | A61M 16/08 482/13 |
| 6,984,214 | B2 * | 1/2006 | Fowler-Hawkins | A61M 16/0006 482/13 |
| 8,653,346 | B2 * | 2/2014 | Schaman | G10D 7/14 84/377 |
| 10,369,408 | B2 * | 8/2019 | Keller | A61M 16/0006 |
| 2004/0158178 | A1 * | 8/2004 | Fowler-Hawkins | A61M 16/08 601/41 |
| 2006/0223675 | A1 * | 10/2006 | Lew | A63D 3/00 482/13 |
| 2013/0036893 | A1 * | 2/2013 | Schaman | G10D 7/14 84/377 |
| 2015/0133810 | A1 * | 5/2015 | Osaki | A61B 5/486 600/538 |
| 2015/0314090 | A1 * | 11/2015 | Wu | A61M 16/0003 128/202.22 |
| 2018/0330702 | A1 * | 11/2018 | Schille | G10H 1/386 |

FOREIGN PATENT DOCUMENTS

| | | |
|---|---|---|
| KR | 10-2018-0095753 A | 8/2018 |
| KR | 10-2019-0081588 A | 7/2019 |
| KR | 10-2113999 B1 | 5/2020 |

OTHER PUBLICATIONS

Korean Office Action for related KR Application No. 10-2021-0096821 mailed Sep. 27, 2021 from Korean Intellectual Property Office.

* cited by examiner

PORTABLE BREATHING MEASUREMENT AND BREATHING EXERCISE DEVICE

CROSS-REFERENCE TO PRIOR APPLICATIONS

This Application is a National Stage Application of PCT International Application No. PCT/KR2021/015324 (filed on Oct. 28, 2021), which claims priority to Korean Patent Application No. 10-2021-0096821 (filed on Jul. 23, 2021), which are all hereby incorporated by reference in their entirety.

BACKGROUND

The present invention relates to a portable breathing measurement and breathing exercise device, and more specifically, to a portable breathing measurement and breathing exercise device, which enables breathing measurement through self-diagnosis to allow safe breathing measurements in pandemic situations such as COVID-19, includes a load control unit to allow customized breathing training for a user, measures the user's breathing capacity or respiratory muscle pressure (MIP, or MEP) in real-time to acquire data by applying information communication technology, guides breathing training according to calculated values considering the user's gender and age based on the acquired data, enables breathing information to be digitized through applications and world wide web to utilize the data in monitoring and diagnosis, and sends alerts to medical personnel in real-time in emergency situations when the user's breathing falls below a predetermined lower limit of normal (LLN) so that the medical personnel can take measures.

Due to the pandemic situation caused by COVID-19 and others, there is a tendency to avoid breathing measurements in hospitals. Accordingly, there is a demand for self-diagnostic breathing measurement devices.

Meanwhile, breathing training is to train patients, who have respiratory difficulties, proper breathing methods in order to alleviate symptoms, such as difficulty in breathing, improve the quality of life, and enhance physical and emotional participation in daily life. Particularly, for patients after lung surgery or patients with chronic obstructive pulmonary disease, breathing training is essential for treatment and recovery.

Moreover, continuous breathing training is essential for respiratory muscle and diaphragm strengthening, lung expansion and stable oxygen supply through inhalation and exhalation training, development of lung capacity and cardiopulmonary function through consistent breathing training, vibrant metabolism through smooth oxygen supply, and participation in leisure/sports activities through cardiopulmonary strengthening.

As an example of conventional breathing measurement devices, Korean Utility Model Registration No. 20-0484020 discloses a precise breathing test device, which can precisely and accurately measure a subject's lung volume to prevent an artificial change and an eddy current phenomenon caused by the Bernoulli effect from occurring on the air exhaled by the subject.

However, such a conventional device cannot guide customized breathing training to each user while measuring the user's breathing capacity, and cannot be continuously used as a portable device.

SUMMARY

Accordingly, the present invention has been made in view of the above-mentioned problems occurring in the related art, and it is an objective of the present invention to provide a portable breathing measurement and breathing exercise device, which enables breathing measurement through self-diagnosis to allow safe breathing measurements in pandemic situations such as COVID-19, includes a load control unit to allow customized breathing training for a user, measures the user's breathing capacity in real-time to acquire data by applying information communication technology, guides breathing training based on the acquired data, enables breathing information to be digitized through applications and world wide web to utilize the data in diagnosis, and sends alerts to medical personnel in real-time in emergency situations when the user's breathing falls below a predetermined lower limit of normal (LLN) so that the medical personnel can take measures.

The aspects of the present invention are not limited to those mentioned above, and other aspects not mentioned herein will be clearly understood by those skilled in the art from the following description.

To accomplish the above-mentioned objects, according to the present invention, there is provided a portable breathing measurement and breathing exercise device including: a body part; a mouthpiece part which is coupled to one side of the main body part; a sensor unit which is provided inside the main body part and measures the pressure of a user's breath through the mouthpiece part; a control unit which receives the measurement values from the sensor unit, stores the measurement value in real-time, analyzes the user's breath based on the measurement value, and provides an exercise schedule; and a display unit which outputs the analysis results and exercise schedule from the control unit, wherein the mouthpiece part includes a load adjusting part which controls the flow of air moving in and out of the mouthpiece part and the main body part due to the user's breath.

Moreover, the mouthpiece part includes: an inlet which is inserted into the user's mouth; a mouthpiece body which is provided at the bottom of the inlet and formed in a cylindrical shape; a filter part which is provided inside the mouthpiece body; and a flexible part which extends from the bottom of the mouthpiece body, and the load adjusting part is provided at the lower portion of the flexible part and is coupled to the upper portion of the main body part.

Furthermore, the main body part includes: a cylindrical part which protrudes upwards from the top of the main body part and has an empty space formed inside; a plurality of slit parts which are provided along the lower outer circumference of the cylindrical part; and a main hole which is formed at least partially through the cylindrical part, and the load adjusting part includes: a coupling part which is formed to surround around the outer circumference of the cylindrical part; a protrusion which is formed on the end of the coupling part to have a shape corresponding to the shape of the plurality of slit parts; and an adjustment hole which is formed at least partially through the coupling part, such that the main body part and the load adjusting part are coupled with each other when the protrusion is inserted into any one of the plurality of slit parts.

Additionally, the control unit includes: a personal web program which receives and stores the measurement values from the sensor unit in real-time; a web server which is linked to the personal web program and receives and stores the measurement values from the sensor unit in real-time; and an administrator web program which is linked to the web server and receives and stores the measurement values from the sensor unit in real-time. The display unit includes: a personal display which outputs the measurement values of the sensor unit; and an administrator display which is located remotely from the personal display and outputs the measurement values of the sensor unit, thereby allowing an administrator to monitor the measurement values of the sensor unit remotely. If the measurement values of the sensor unit fall below a preset threshold or are not transmitted for a preset duration, the control unit sends an alarm signal to the administrator web program and controls the output of the alarm signal to the administrator display.

In addition, each of the personal display and the administrator display includes: an application which receives and stores measurement values from the sensor unit in real-time, analyzes the user's breath based on the measurement values of the sensor unit, and supports breathing exercise. The sensor units are provided in plural, and are respectively linked to the personal web program, the administrator web program, and the application. Each of the personal web program, the administrator web program, and the application stores information data of at least one reference sensor unit, and corrects the measurement values of the sensor units according to the state of the load adjusting part corresponding to each of the plurality of sensor units, thereby minimizing a measurement error between the different sensor units.

The portable breathing measurement and breathing exercise device according to the present invention enables breathing measurement through self-diagnosis to allow safe breathing measurements in pandemic situations such as COVID-19, includes a load control unit to allow customized breathing training for a user, and can measure the user's breathing capacity in real-time to acquire data by applying information communication technology, and guide breathing training based on the acquired data.

Moreover, the portable breathing measurement and breathing exercise device according to the present invention can adjust the intensity of breathing exercise by setting the main hole and the adjustment hole to communicate or not to communicate with each other as the protrusion is inserted into any one of the plurality of slit parts.

Furthermore, the portable breathing measurement and breathing exercise device according to the present invention can enhance inspiratory muscle strength and endurance, increase diaphragmatic thickness, increase cardiac output, increase maximum oxygen consumption, prolong the time to exhaustion, and improve lactate decomposition ability.

Additionally, the portable breathing and measurement breathing exercise device according to the present invention can monitor the state of breathing exercise in real-time.

In addition, the portable breathing measurement and breathing exercise device according to the present invention allows users to continue breathing exercises and measurements without being bored through applications, and enables children to be interested and actively participate in breathing exercises and measurements.

The advantages of the present invention are not limited to the above-mentioned advantages, and other advantages, which are not specifically mentioned herein, will be clearly understood by those skilled in the art from the following description.

BRIEF DESCRIPTION OF THE DRAWINGS

FIG. 4, (b) is a side view of the main body part of the portable breathing measurement and breathing exercise device according to an embodiment of the present invention.

FIG. 5, (b) is a view illustrating the state in which the main hole and the adjustment hole of the portable breathing measurement and breathing exercise device are coupled to communicate with each other according to an embodiment of the present invention.

DETAILED DESCRIPTION

Figure 1:
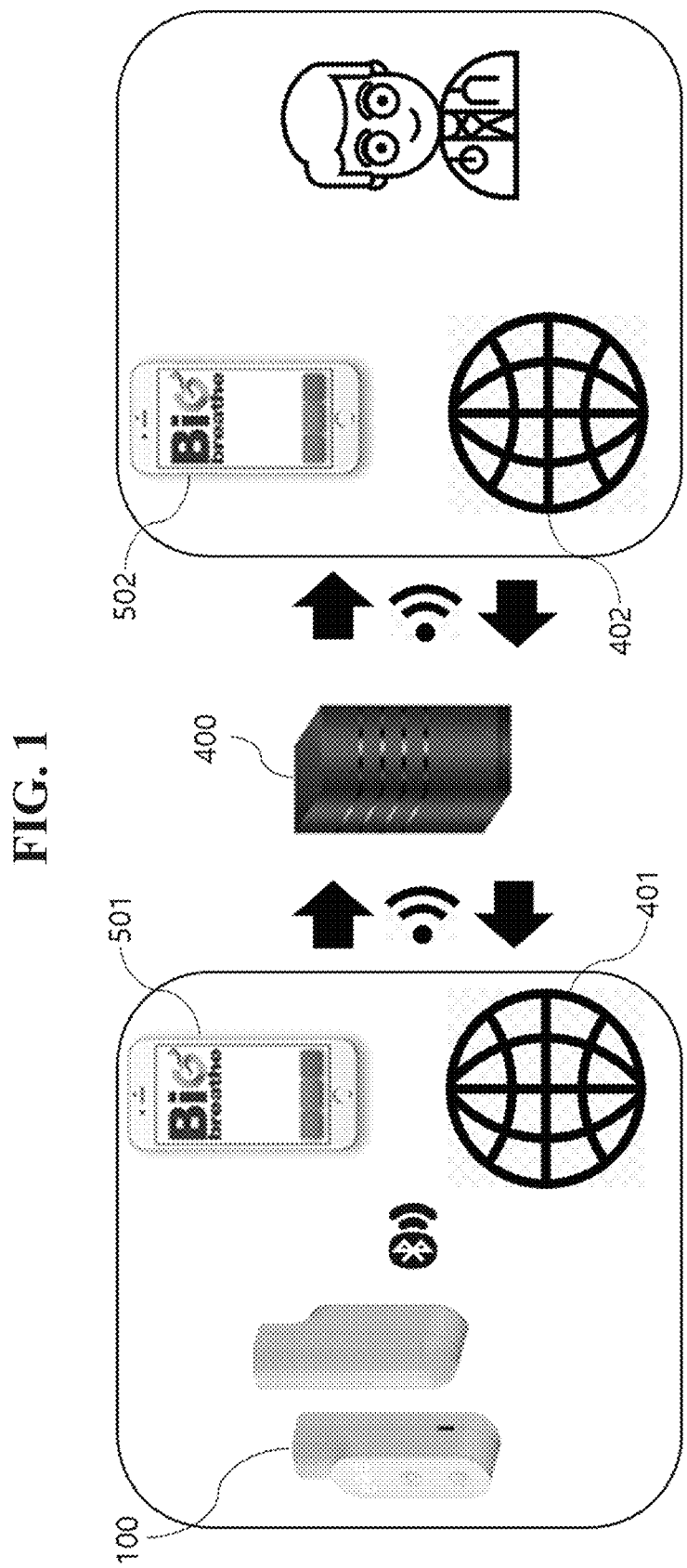
FIG. 1 is a configuration diagram of a portable breathing measurement and breathing exercise device according to an embodiment of the present invention.
Figure 2:
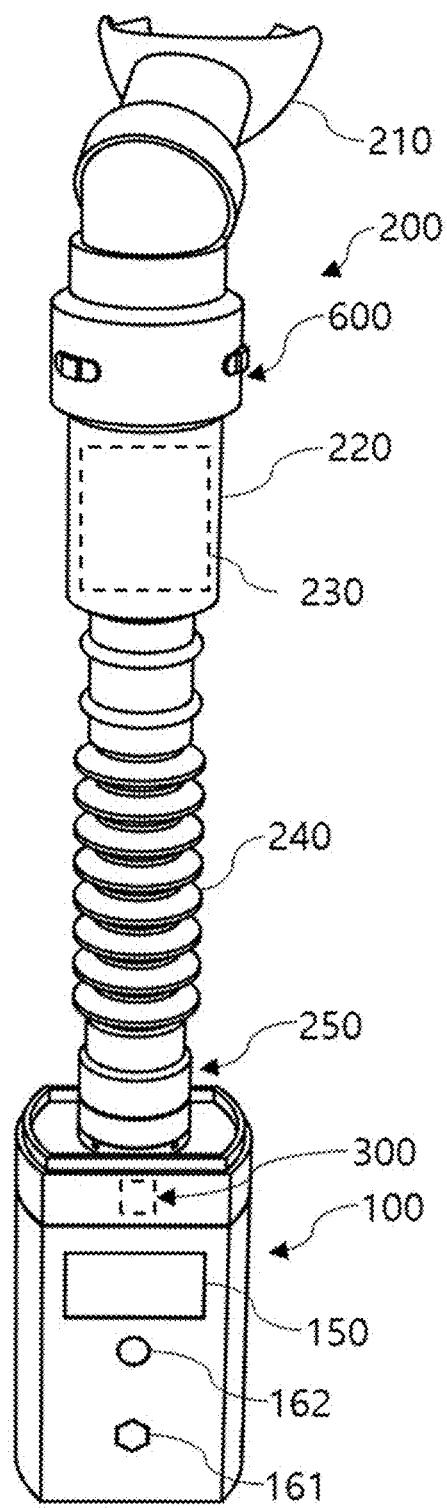
FIG. 2 is a view illustrating a main body and a mouthpiece part of the portable breathing measurement and breathing exercise device according to an embodiment of the present invention.
Figure 3:
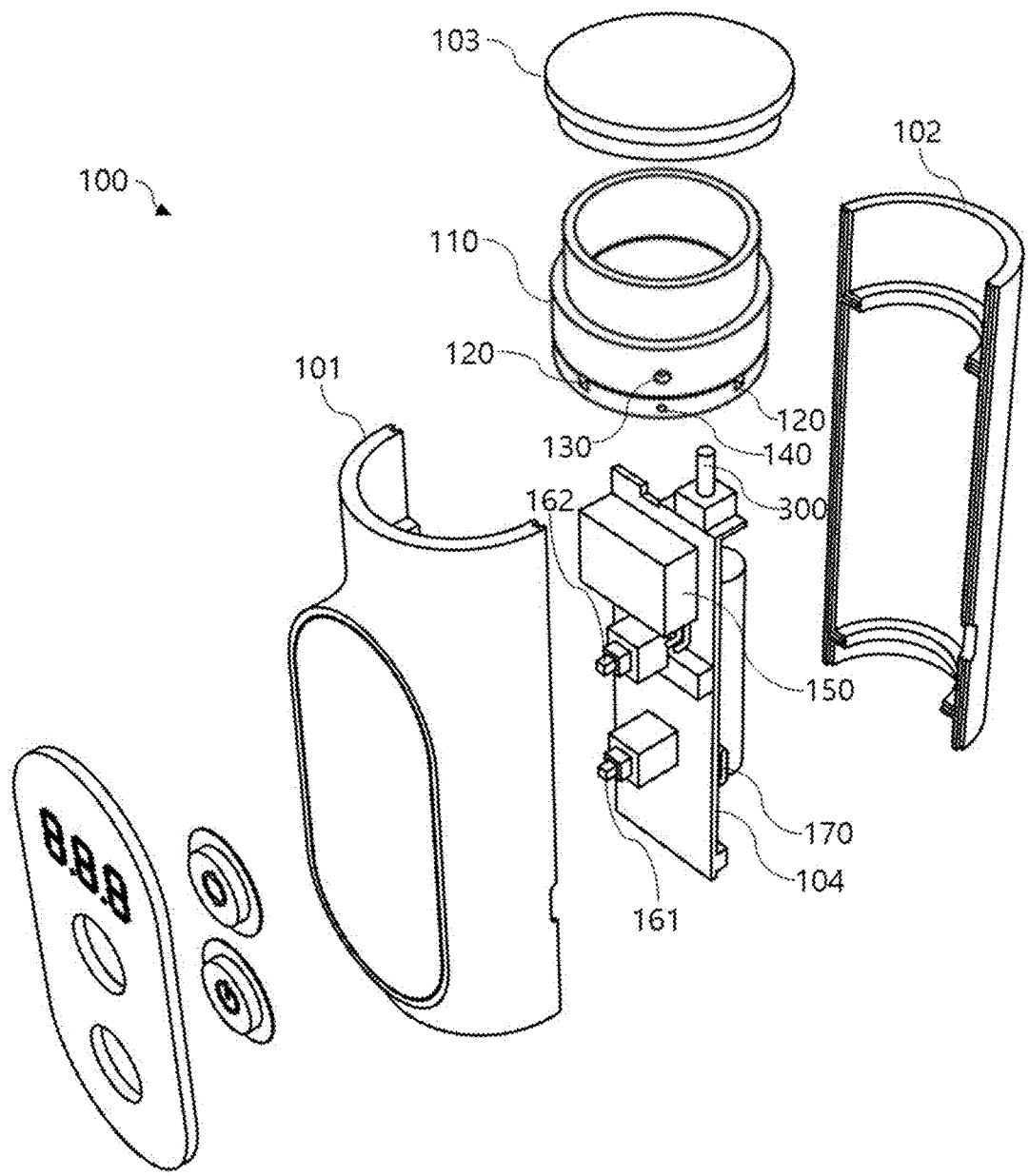
FIG. 3 is an exploded view illustrating the configuration of the main body part of the portable breathing measurement and breathing exercise device according to an embodiment of the present invention.
Figure 4:
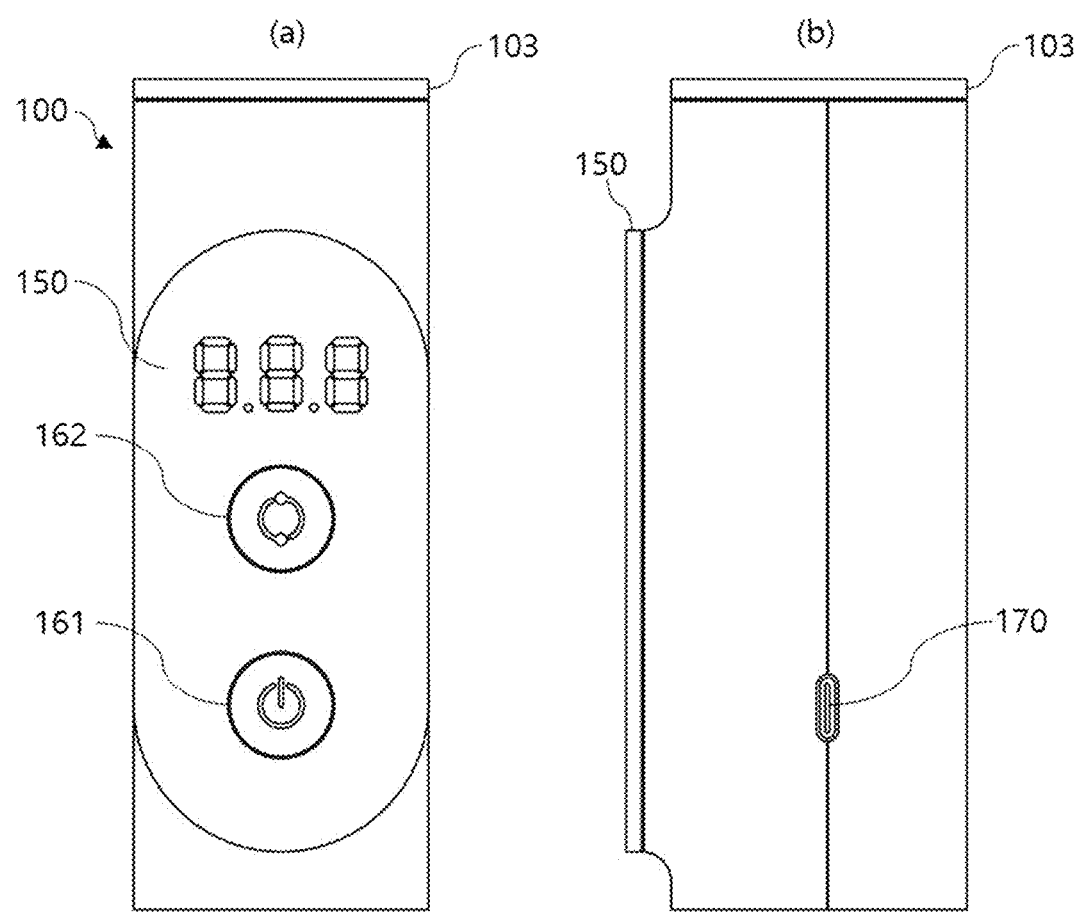
FIG. 4, (a) is a front view of the main body part of the portable breathing measurement and breathing exercise device according to an embodiment of the present invention.

The terms used in the present specification will be explained in brief, and the present invention will be described in detail.

The terms used in the present invention have been chosen to be the general terms currently widely used, while considering the functions in the present invention. However, the terms may be changed depending on the intent of technicians in the field, precedents, or the emergence of new technologies. Therefore, the terms used in the present invention should be defined not just by the name of the term, but based on the meanings of the terms and the contents of the present invention as a whole.

In the entire specification of the present invention, when any portion "includes" any component, this does not exclude other components but means that any other component can be further included, unless stated otherwise.

Hereinafter, the embodiments of the present invention will be described in detail with reference to accompanying drawings so that the embodiments may be easily implemented by those skilled in the art. However, the present invention may be implemented in various ways without being limited to the embodiments.

Specific details including the technical problem, the technical solution, and the advantageous effects are included in the embodiments and drawings described below. The advantages and features of the present invention and the methods of achieving them will become clear with reference to the embodiments described in detail with the accompanying drawings.

Hereinafter, the present invention will be described in more detail with reference to the attached drawings.

Referring to FIGS. 1 through 9, a portable breathing measurement and breathing exercise device according to a preferable embodiment of the present invention includes: a main body part 100; a mouthpiece part 200 which is coupled to one side of the main body part 100; a sensor unit 300 which is provided inside the main body part 100 and measures the pressure of a user's breath through the mouthpiece part 200; a control unit 400 which receives the measurement values from the sensor unit 300, stores the measurement value in real-time, analyzes the user's breath based on the measurement value, and provides an exercise schedule; and a display unit 500 which outputs the analysis results and exercise schedule from the control unit 400.

First, the main body part 100 is provided. The main body part 100 has an empty space inside and is formed to have an overall elliptical cross-section. For example, referring to FIGS. 2 and 3, the main body part 100 includes a left case 101, a right case 102 which has a shape corresponding to the left case 101 and is coupled to the left case 101, and caps 103 which are respectively coupled to the upper and lower portions of the left case 101 and the right case 102.

Moreover, the main body part 100 has a board 104 provided therein, and a display part 150, a power switch 161, an operation switch 162, and a charging terminal 170 can be provided on the board 104. Here, the display part 150 is provided on the front surface of the left case 101 to display the measurement values of the sensor unit 300, the power switch 161 turns on and off the supply of power to the display part 150 and the operation switch 162, the operation switch 162 allows setting the start and the end of breathing measurement and breathing exercise, and the charging terminal 170 allows charging a battery (not illustrated) which supplies power to the display part 150, the power switch 161, and the operation switch 162.

Next, the mouthpiece part 200 is provided. The mouthpiece part 200 includes: an inlet 210 which is inserted into the user's mouth; a mouthpiece body 220 which is provided at the bottom of the inlet 210 and formed in a cylindrical shape; a filter part 230 which is provided inside the mouthpiece body 220; and a flexible part 240 which extends from the bottom of the mouthpiece body 220.

More specifically, the inlet 210 is inserted into the user's mouth during breathing measurement and exercise and allows the user's inspiration or expiration to flow to the sensor unit 300. At this time, the inlet 210 is formed of a material which is harmless to the human body, and is designed to be easily assembled and disassembled to prevent the user's body fluid from being transferred to another user. That is, the inlet 210 can be selectively inserted into and coupled with the mouthpiece body 220.

Furthermore, the mouthpiece body 220 has a tube therein to allow the flow of the user's inhalation or exhalation, and is made of a rigid material to prevent the inhalation or the exhalation from leaking outside or shaking during the inhalation or the exhalation. Moreover, inside the mouthpiece body 220, there is a filter part 230 which prevents the user's saliva or external foreign substances from being transmitted to the sensor unit 300. In this instance, the filter part 230 may be a bacterial filter to prevent the user's saliva or bacteria from being transmitted to other users. Additionally, the filter part 230 may be made of synthetic fibers, natural fibers, or other various materials. The filter part 230 filters out foreign substances and harmful materials contained in the air passing through the inlet 210, thereby transmitting only clean air into the main body part 100, and enabling hygienic use. The filter part 230 also filters the user's breath to enable more accurate measurement of the breath.

Moreover, the flexible part 240 is made of an elastic material and is formed to be rotatable, thereby making it easily accessible to the user's mouth during use. In this instance, the mouthpiece body 220 is formed to be adjustable in length, thereby facilitating easy reach to the user's mouth during use. In other words, the inlet 210 can easily reach the user's mouth without movement of the main body part 100, thereby facilitating smoother breathing exercises and breathing measurements.

On the other hand, the mouthpiece part 200 includes a load adjusting part 250 which controls the flow of air moving in and out of the mouthpiece part 200 and the main body part 100 due to the user's breath. The load adjusting part 250 is provided at the lower portion of the flexible part 240 and is coupled to the upper portion of the main body part 100.

Figure 5:
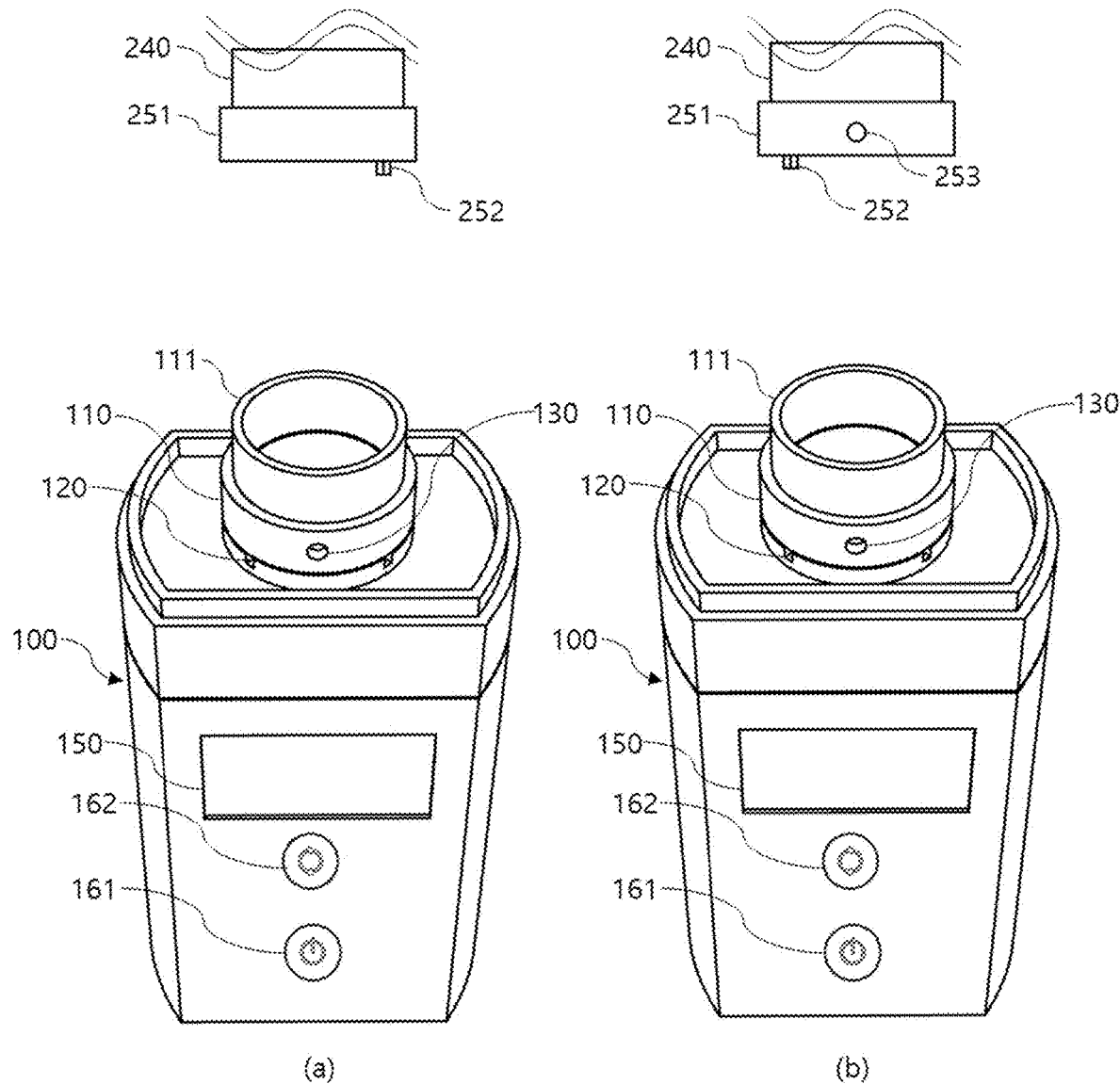
FIG. 5, (a) is a view illustrating a state in which a main hole and an adjustment hole of the portable breathing measurement and breathing exercise device are coupled so as not to communicate with each other according to an embodiment of the present invention.
Figure 6:
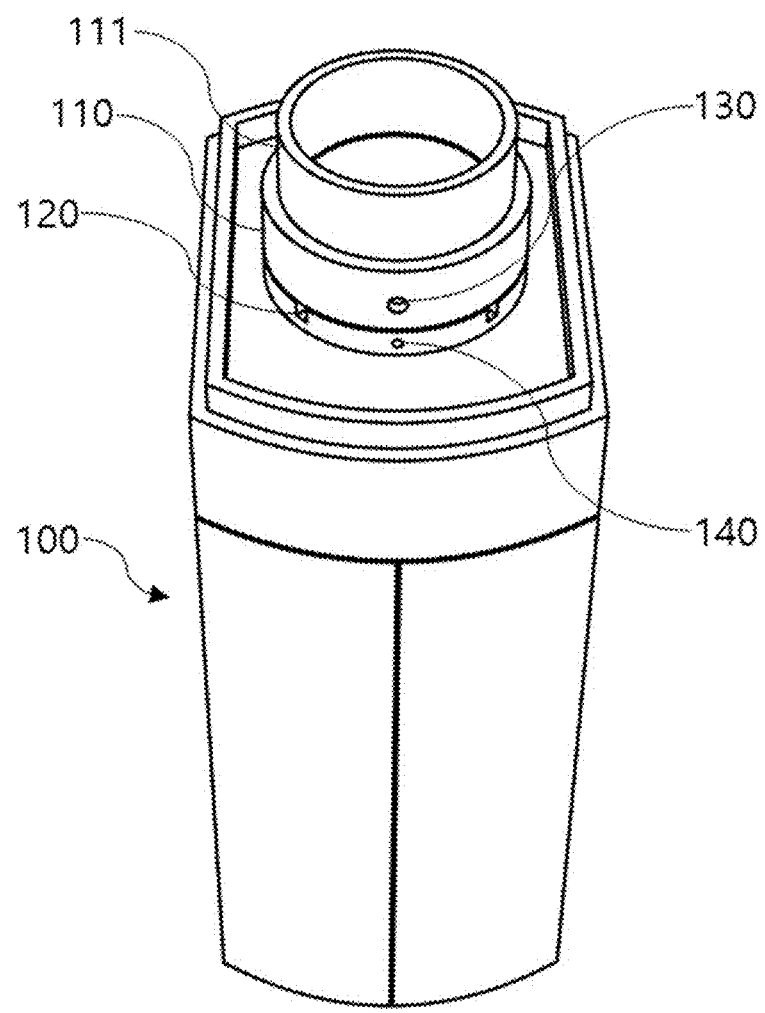
FIG. 6 is a side perspective view illustrating the configuration of the main body part of the portable breathing measurement and breathing exercise device according to an embodiment of the present invention.

More specifically, referring to FIGS. 5 and 6, the main body part 100 includes: a cylindrical part 110 which protrudes upwards from the top of the main body part 100 and has an empty space formed inside; a plurality of slit parts 120 which are provided along the lower outer circumference of the cylindrical part 110; and a main hole 130 which is formed at least partially through the cylindrical part 110.

First, the cylindrical part 110 is inserted into a coupling part 251, which will be described later, to communicate with the coupling part, such that the user's inhalation or exhalation flowing through the inlet 210 can move into the interior of the main body part 100 and reach the sensor unit 300. In addition, the plurality of slit parts 120 are radially arranged around the center of the cylindrical part 110, and are formed alternately with the main hole 130. In this instance, a protrusion 252, which will be described later, is inserted into the slit parts 120, such that the load adjusting part 250 and the main body part 100 can be fixed. Furthermore, the main hole 130 is formed in the center of the cylindrical part 110, and allows at least a portion of the user's inhalation or exhalation flowing through the inlet 210 to leak outside when communicating with the adjustment hole 253. In other words, when the main hole 130 and the adjustment hole 253 communicate, more intense breathing training can be conducted.

The load adjusting part 250 includes: a coupling part 251 which is formed to surround around the outer circumference of the cylindrical part 110; a protrusion 252 which is formed on the end of the coupling part 251 to have a shape corresponding to the shape of the plurality of slit parts 120; and an adjustment hole 253 which is formed at least partially through the coupling part 251, such that the main body part 100 and the load adjusting part 250 are coupled with each other when the protrusion 252 is inserted into any one of the plurality of slit parts 120.

First, the coupling part 251 has an empty space formed inside, and has an inner circumference corresponding to the outer circumference of the cylindrical part 110. The protrusion 252 protrudes downwards from the coupling part 251, and is eccentrically formed from the center of the coupling part 251. As the cylindrical part 110 is inserted into the coupling part 251 and the protrusion 252 is inserted into the slit part 120, the load adjusting part 250 and the main body part 100 are coupled. In this instance, the cylindrical part 110 may further include a guide part 111 which protrudes upwards from the inner surface to facilitate the insertion into the coupling part 251. The guide part 111 serves to guide the cylindrical part 110 into the coupling part 251 more easily. Additionally, the adjustment hole 253 is formed in the center of the coupling part 251, and allows at least a portion of the user's inhalation or exhalation flowing through the inlet 210 to leak outside when communicating with the adjustment hole 253. In other words, when the main hole 130 and the adjustment hole 253 communicate, more intense breathing training can be conducted.

In other words, when the protrusion 252 is inserted into any one of the multiple slit parts 120, the main hole 130 and the adjustment hole 253 can communicate with each other. Here, the longitudinal length of the cylindrical part 110 is formed to be equal to the longitudinal length of the coupling part 251, and the main hole 130 and the adjustment hole 253 are formed to correspond to each other at the central portion of the cylindrical part 110 and at the central portion of the coupling part 251, respectively. Additionally, the length ranging from the protrusion 252 to the adjustment hole 253 is formed to be the same and correspond to the length ranging from the slit part 120 to the main hole 130. Therefore, as illustrated in FIG. 5, (a), when the cylindrical part 110 is inserted into the coupling part 251 in the state in which the adjustment hole 253 is positioned at the rear, the main hole 130 is closed so that the user's inhalation or exhalation does not leak outside. Conversely, as illustrated in FIG. 5, (b), when the mouthpiece part 200 is rotated with the adjustment hole 253 positioned at the front and the cylindrical part 110 is inserted into the coupling part 251, the main hole 130 and the adjustment hole 253 communicate with each other so that at least a portion of the user's inhalation or exhalation flowing through the inlet 210 leaks outside. As described above, when the protrusion 252 is inserted into any one of the plurality of slit parts 120, the intensity of breathing exercises can be adjusted.

Consequently, as illustrated in FIG. 5, (a), when the cylindrical part 110 is inserted into the coupling part 251 in the state in which the adjustment hole 253 is located at the rear, the main hole 130 is closed and the user's inhalation or exhalation does not leak outside, thereby achieving more accurate breathing measurement. Furthermore, as illustrated in FIG. 5, (b), when the mouthpiece part 200 is rotated in the state in which the adjustment hole 253 is positioned at the front and the cylindrical part 110 is inserted into the coupling part 251, the main hole 130 and the adjustment hole 253 communicate with each other such that at least a portion of the user's inhalation or exhalation flowing through the inlet 210 leaks outside, thereby facilitating more intense breathing exercises.

Referring to FIG. 6, the main body part 100 further includes a plurality of sub-holes 140 provided along the lower outer circumferential surface of the cylindrical part 110, and the plurality of sub-holes 140 are provided alternately with the plurality of slit parts 120. The plurality of sub-holes 140 are arranged radially around the center of the cylindrical part 110. For example, the sub-holes 140 may be spaced at 90-degree angles around the center of the cylindrical part 110 relative to adjacent sub-holes. Here, the plurality of sub-holes 140 are provided on the same circumference of a virtual circle as the plurality of slit parts 120, such that at least a portion of the user's inhalation and exhalation always leaks outside. That is, the plurality of sub-holes 140 function to prevent damage to the sensor unit 300 and other components from sudden pressure changes inside the main body part 100 and mouthpiece part 200 due to the user's breath.

Figure 7:
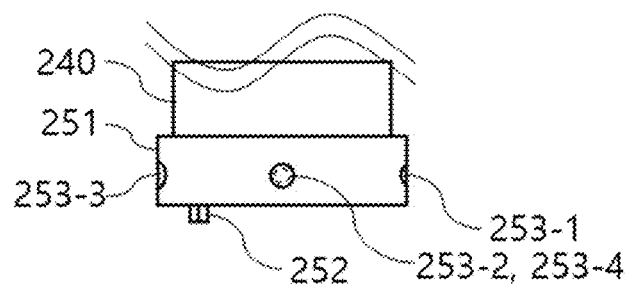
FIG. 7 is a view illustrating a plurality of adjustment holes of a portable breathing measurement and breathing exercise device according to another embodiment of the present invention.
Figure 7:
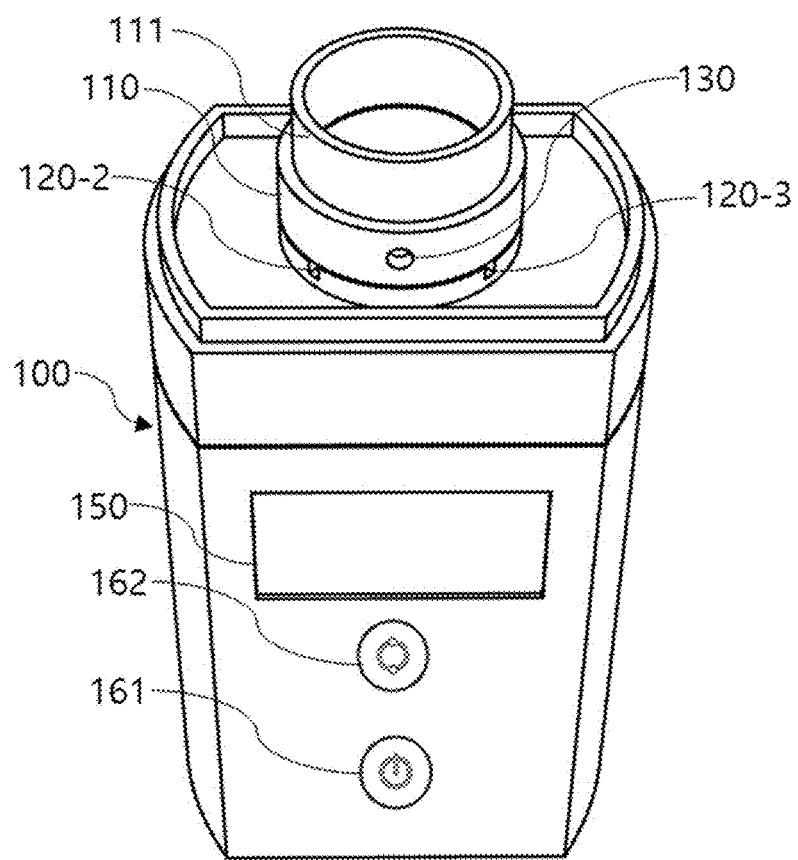
Figure 8:
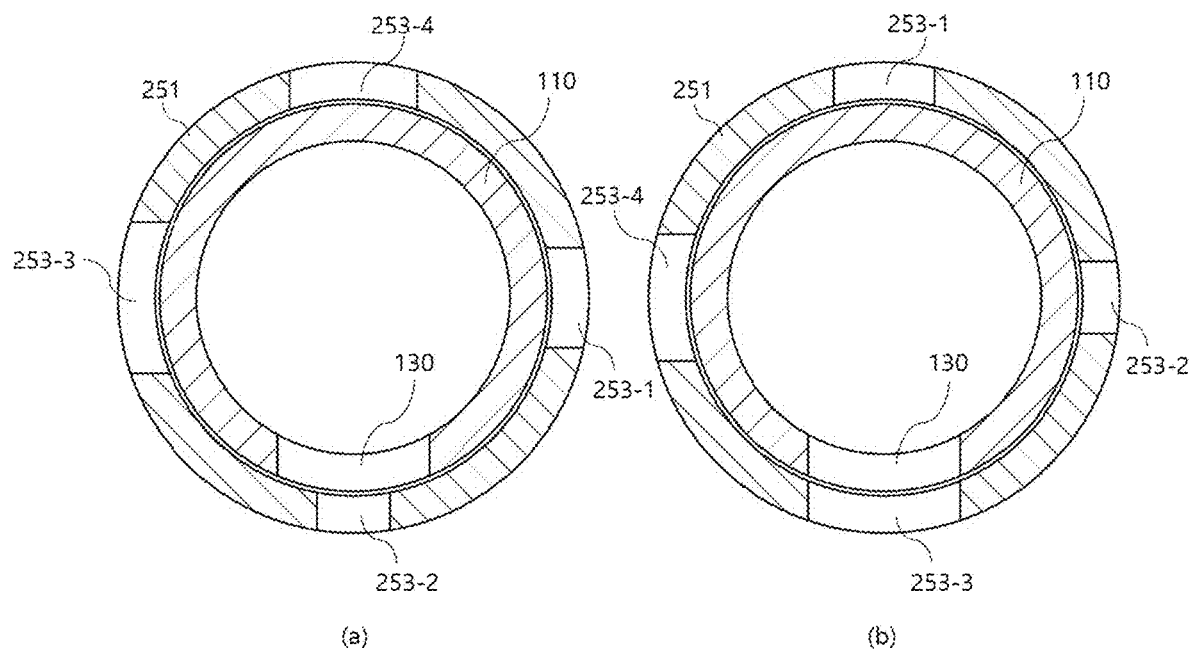
FIG. 8 is a sectional view illustrating a plurality of adjustment holes of a portable breathing measurement and breathing exercise device according to another embodiment of the present invention.
Figure 9:
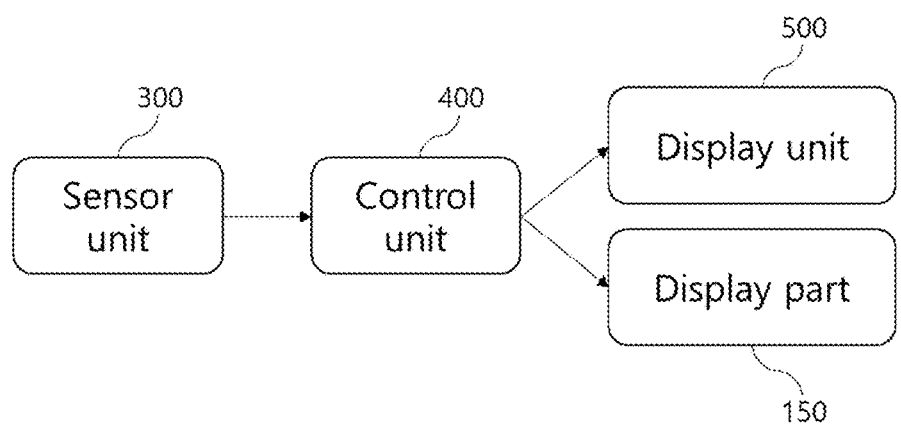
FIG. 9 is a view illustrating a control configuration of the portable breathing measurement and breathing exercise device according to an embodiment of the present invention.

Next, referring to FIGS. 7 and 8, the plurality of adjustment holes 253 are arranged radially based on the center of the coupling part 251. For example, the adjustment holes 253 may be provided at 90-degree angles to each adjacent adjustment hole 253 centered on the coupling part 251. Moreover, the plurality of adjustment holes 253 can be formed to have different diameters. For example, the plurality of adjustment holes 253 can be arranged in such a way that the diameter of the adjustment hole 253 located at the front surface gradually increases as the coupling part 251 rotates clockwise. In this instance, diameter of each of the plurality of adjustment holes 253 is formed to be equal to or less than the diameter of the main hole 130.

Moreover, the slit parts 120 can be formed at 90-degree intervals around the center of the cylindrical part 110 relative to adjacent slit parts. As a result, when the protrusion 252 is inserted into one of the plurality of slit parts 120, one of the plurality of adjustment holes 253 communicates with the main hole 130. For example, when the protrusion 252 is inserted into the second slit part 120-2, the main hole 130 communicates with the second adjustment hole 253-2, and when the protrusion 252 is inserted into the third slit part 120-3, the main hole 130 communicates with the third adjustment hole 253-3. As described above, when the protrusion 252 is inserted into any one of the multiple slit parts 120, the intensity of breathing exercises can be adjusted more minutely in stages.

Next, the control unit 400 receives measurement values from the sensor unit 300, stores them in real-time, analyzes the user's breath based on the values, and provides an exercise schedule. For example, the control unit 400 may be a public institution server away from the sensor unit 300, and if the measurement value from the sensor unit 300 falls below the minimum standard for respiratory muscles, may generate an alarm signal to prompt a visit to a hospital or a similar facility. Therefore, the control unit 400 allows for the safe performance of breathing measurements through self-diagnosis in pandemic situations like COVID-19. Furthermore, the sensor unit 300 has a GPS function to periodically transmit the location of the relevant sensor unit 300, thereby allowing the public institution server to track the location of the sensor unit 300. Additionally, the sensor unit 300 may be a pressure sensor, which measures the pressure of the flow of the user's inhalation or exhalation and transmits the measurement values to the control unit 400. In addition, a display unit 500 serves to output the analysis results and exercise schedule from the control unit 400.

In more detail, the sensor unit 300 is attached to and detached from the board 104, and serves to measure and transmit the user's breathing pattern. That is, the sensor unit 300 serves to measure the pressure and the flow rate of the user's inhalation or exhalation, and can have any form as long as it can measure the pressure and the flow rate of the user's inhalation or exhalation. For example, the sensor unit 300 may be a pressure sensor which measures the user's lung volume.

In this instance, the sensor unit 300 includes a communication part (not illustrated) that transmits the measurement values of the sensor unit 300 to a terminal device, and the display unit 500 can include an application 510 that analyzes the user's breathing pattern measurement values received from the communication part. The communication part can perform wireless communication using Bluetooth, WiFi, NFC, etc. The application 510 analyzes the user's breath based on the measurement values, and provides an appropriate exercise schedule for the user. Additionally, the application 510 can display analysis results and exercise schedules.

In addition, the sensor unit 300 can include: a light-emitting part (not illustrated) that indicates the charging status and the operational status of the sensor unit 300; and a supply part (not illustrated) that supplies power to the sensor unit 300.

In more detail, the light-emitting part may be an LED lamp which emits light in different colors according to the charging status or the operational status of the sensor unit 300, thereby allowing the user to easily check the status visually. For example, the light-emitting part does not emit light ordinarily but lights up in a predetermined color when the user measures inhalation or exhalation, to indicate that the breathing measurement is in progress.

Additionally, the communication part is provided to transmit and receive wireless signals with one or more external devices, and can include at least one of a Bluetooth chip, a WiFi chip, an NFC chip, or a wireless communication chip (such as an LTE chip). According to an embodiment of the invention, the communication part may use a Bluetooth chip for near-field communication with an external terminal, but it is just an example, and long-distance communication methods could also be used for communication with the terminal.

Moreover, the supply part may include one or more rechargeable batteries built-in for power supply or a power module that can receive external power through a wired connection.

Furthermore, the control unit 400 includes: a personal web program 401 which receives and stores the measurement values from the sensor unit 300 in real-time; a web server (not illustrated) which is linked to the personal web program 401 and receives and stores the measurement values from the sensor unit 300 in real-time; and an administrator web program 402 which is linked to the web server and receives and stores the measurement values from the sensor unit 300 in real-time. In addition, the display unit 500 includes: a personal display 501 which outputs the measurement values of the sensor unit 300; and an administrator display 502 which is located remotely from the personal display 501 and outputs the measurement values of the sensor unit 300, thereby allowing an administrator to monitor the measurement values of the sensor unit 300 remotely. In this instance, if the measurement values of the sensor unit 300 fall below a preset threshold or are not transmitted for a preset duration, the control unit 400 sends an alarm signal to the administrator web program 402 and controls the output of the alarm signal to the administrator display 502. As a result, it allows for remote monitoring of users, such as patients with pulmonary surgery and patients with respiratory diseases, and allows real-time monitoring, especially for socially vulnerable groups such as the elderly living alone. Moreover, if the measurement values from the sensor unit 300 fall below a preset threshold or are not transmitted for a preset duration, it can induce visit of medical personnel and caregivers, thereby allowing for immediate action to be taken. The data stored in the administrator web program can be used as reference material for the diagnosis and treatment of the respective user.

Additionally, the application 510 is provided. The application 510 can analyze the user's breathing based on the measurement values from the sensor unit 300 and provide an appropriate exercise schedule for the user.

Moreover, the application 510 enables the exercise schedule management, the exercise status feedback, the analysis of exercise results, and the calorie consumption by breathing exercises to be output to a terminal such as the user's smartphone, based on the user's breathing information transmitted from the communication part. In this instance, the application 510 can serve to output analysis results and exercise schedules. That is, the application 510 can digitally display the user's lung volume through the value calculated by the sensor unit 300, and the exercise schedule management, the exercise status feedback, and the analysis of exercise results can be output to the user's device, such as a smartphone, by the application 510.

In addition, the application 510 also allows the user to receive and verify the exercise schedule management, the exercise status feedback, and the analysis of exercise results in real-time. For instance, after the user logs in to the smart app, the user can perform breathing exercises, measure maximum inspiration pressure and maximum expiration pressure, and check the user's usage records.

For example, through the screen of the application 510, the user registers the user's information, pressure values, and exercise type. In this instance, the user information can be divided and stored in plural, and the exercise types could include, for example, fitness, jogging, and cycling. After registering the user information, the user proceeds with breathing exercises and measurements by executing tabs for GPS, calorie consumption, and breathing pattern. Here, the sensor unit 300 may include a GPS sensor for measuring the location of the sensor unit 300.

Furthermore, when the user executes the breathing pattern tab, the user can check information such as the best record, and the average record, and for example, the most recent five breathing exercises and measurement values can be output. The application generates a graph with time on the horizontal axis and pressure on the vertical axis to calculate an average value, thereby facilitating an overview of recent breathing exercises and measurements at a glance. The created graph can be automatically stored as a file, and can be transmitted and received. Finally, the application outputs the user's strengths and weaknesses, and proposes methods for reproducing the optimal breathing graph shape.

Additionally, when the user executes the calorie consumption tab, the stored breathing exercise and measurement values are displayed in a time-sequenced manner. For example, when the user clicks on an exercise duration of 30 seconds, information, such as maximum inspiration pressure, average inspiration pressure, maximum expiration pressure, average expiration pressure, and total exercise time, can be displayed. In this instance, breathing exercises and measurements are automatically recorded if the user does exercise for longer than three seconds.

Moreover, when the user executes the GPS tab, the user's travel distance and route, and the user's location at different times of workout can be displayed.

Referring to FIGS. 10 through 13, the application 510 may include a recent record window 511, a detailed measurement result window 512, a summary result window 513, a result graph window 514, a correction setting window 515, a breathing exercise control window 516, a real-time breathing exercise result window 517, and a final breathing exercise result window 518.

Figure 10:
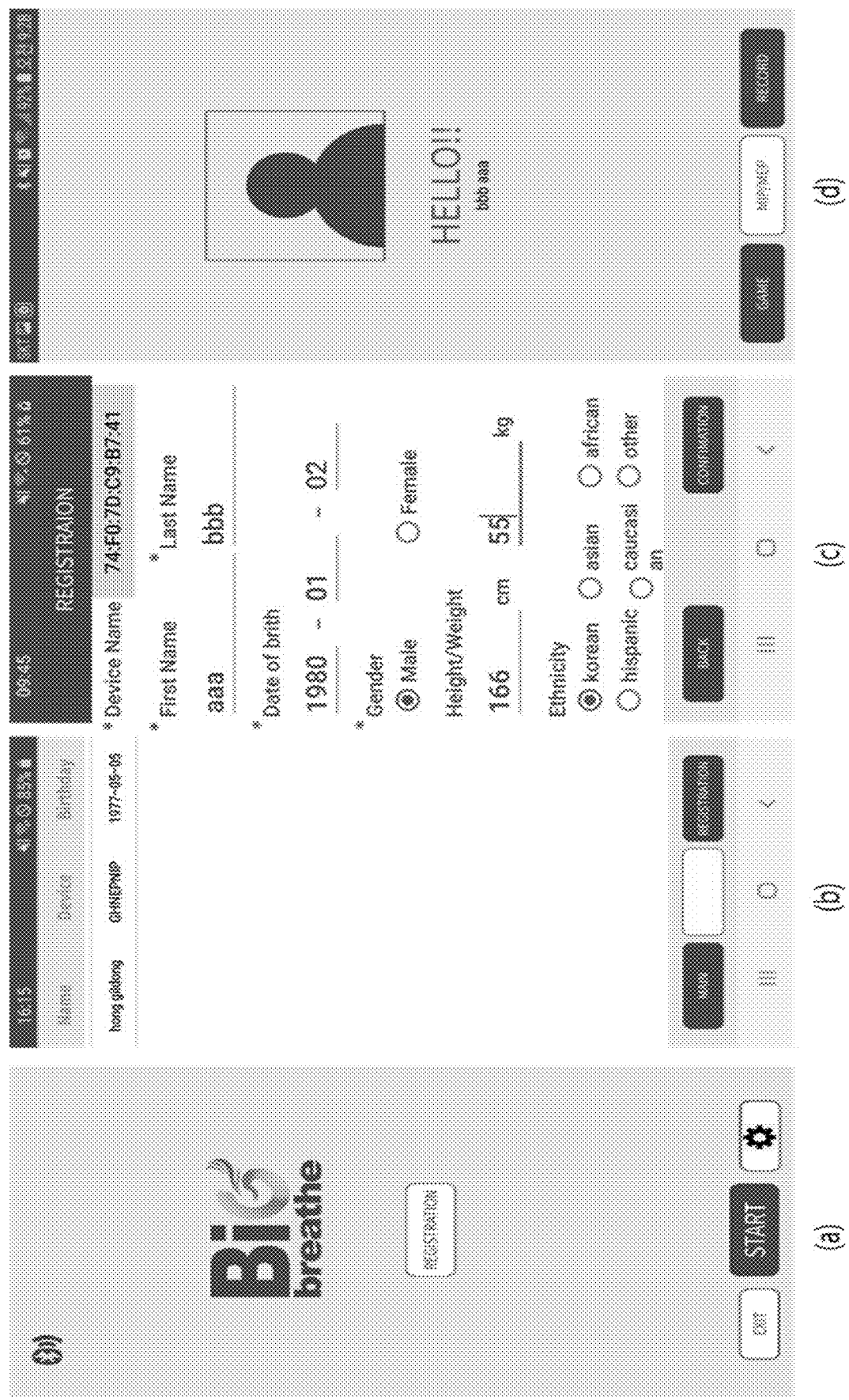
FIGS. 10 and 11 are views illustrating a screen of a display part or an application of the portable breathing measurement and breathing exercise device according to an embodiment of the present invention.

In more detail, as illustrated in FIG. 10, (a), the user can perform user registration and Bluetooth pairing through a REGISTRATION button, and perform settings, such as user manual, glossary, and language selection, through a sawtooth button. In addition, referring to FIG. 10, (b), when proceeding as a pre-registered user, the user touches the list on the user selection screen, and when the user wants to change the information of the pre-registered user, the user touches the screen till a change button and a delete button are popped up. Moreover, the user can perform new user registration and new Bluetooth pairing through the REGISTRATION button. Referring to FIG. 10, (c), the sections marked with a red star indicate mandatory fields that must be filled for saving. Lastly, referring to FIG. 10, (d), the user can perform breathing exercises through an EXERCISE button, perform breathing measurements through an MIP/MEP button, and check stored data through a RECORD button. In this instance, the RECORD button is optional, and a window generated through the EXERCISE and RECORD buttons can include a RECORD button.

Figure 11:
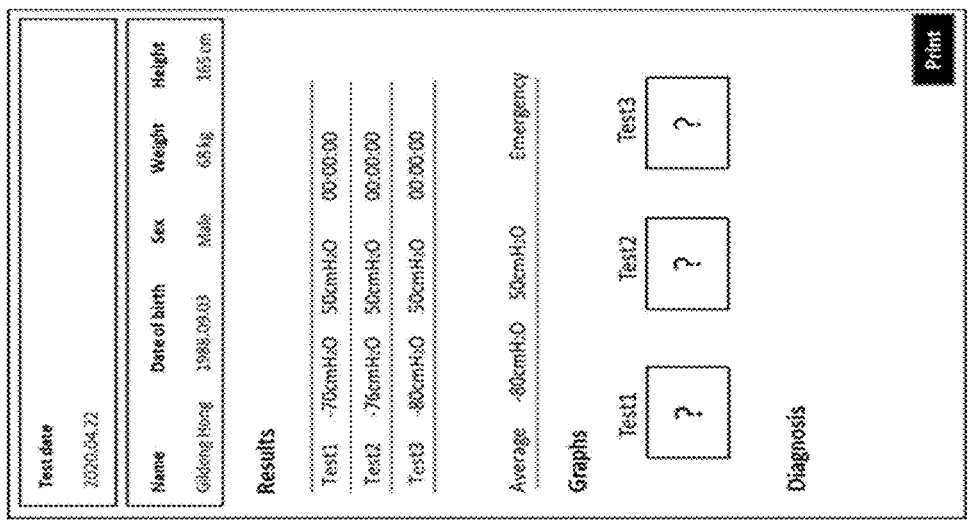
Figure 11:
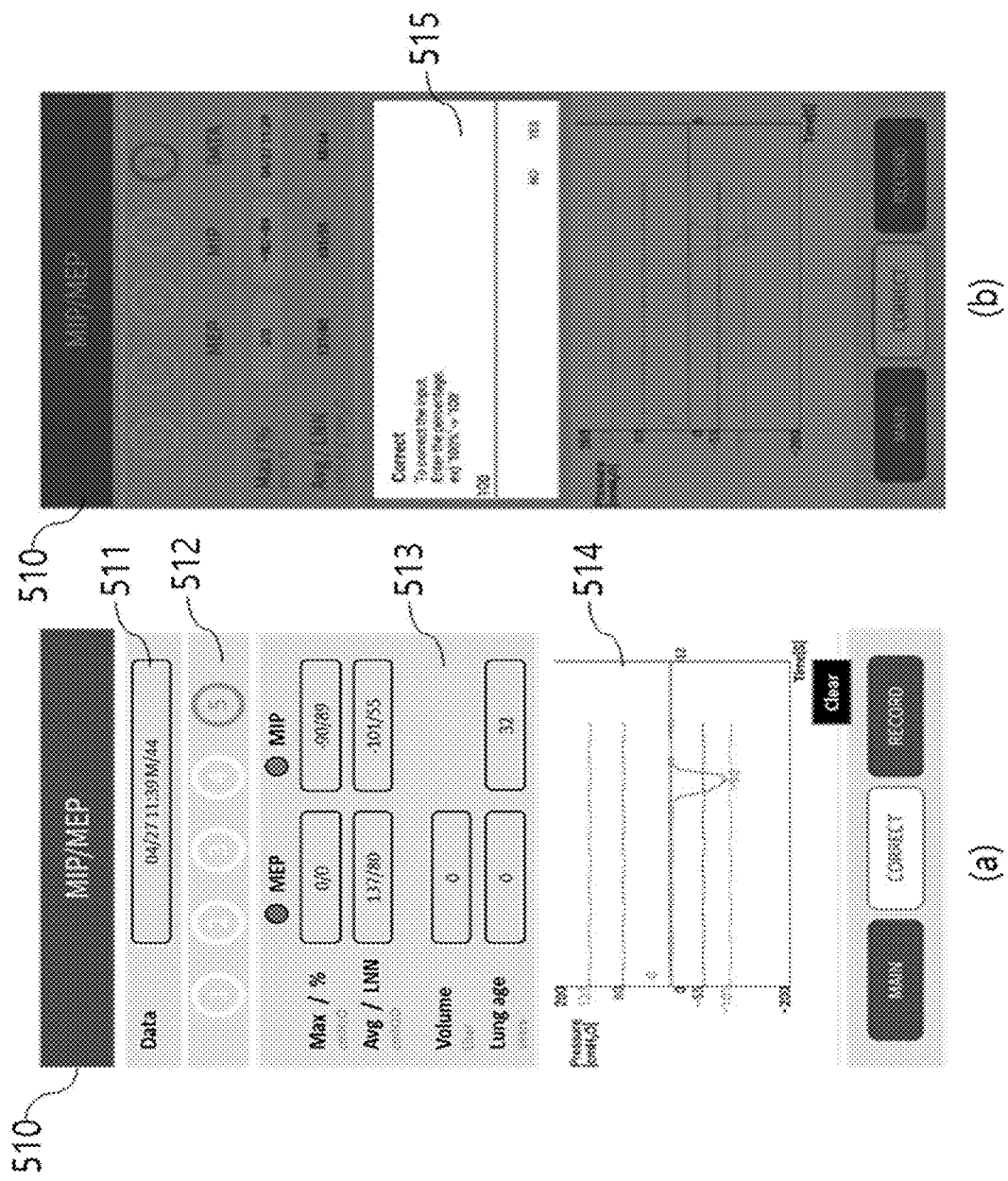

Referring to FIG. 11, (a), the application 510 can produce different sounds for the start, end, and during breathing measurement or exercise. At the top screen of the application 510, a " " mark for entering a help window which explains the terms of MIP/MEP can be formed, and the terms on the window all have the " " mark for entering a help window which explains the relevant terms. In addition, for recent record window 511, a test to be reflected in Report can be selected by pressing for more than one second, and the selected Test may be indicated in a specific color. Five records can be saved and reviewed, and the currently reviewed test result is marked in orange. When returning from a TECORD button, reset is not executed, and a clear button having a reset function can be formed. Furthermore, the detailed measurement result window 512 can select and output only a desired test result when the user clicks any one among a plurality of MIP/MEP test results, and can be linked with a printer. Furthermore, when the user clicks any one among the plurality of MIP/MEP test results to select the desired test result, a graph corresponding to the selected test result is displayed at the lower portion like the result graph window 514. Moreover, a CORRECT button allows for correction. A popup window inducing a hospital visit when respiratory muscle status is at risk may be displayed.

Figure 12:
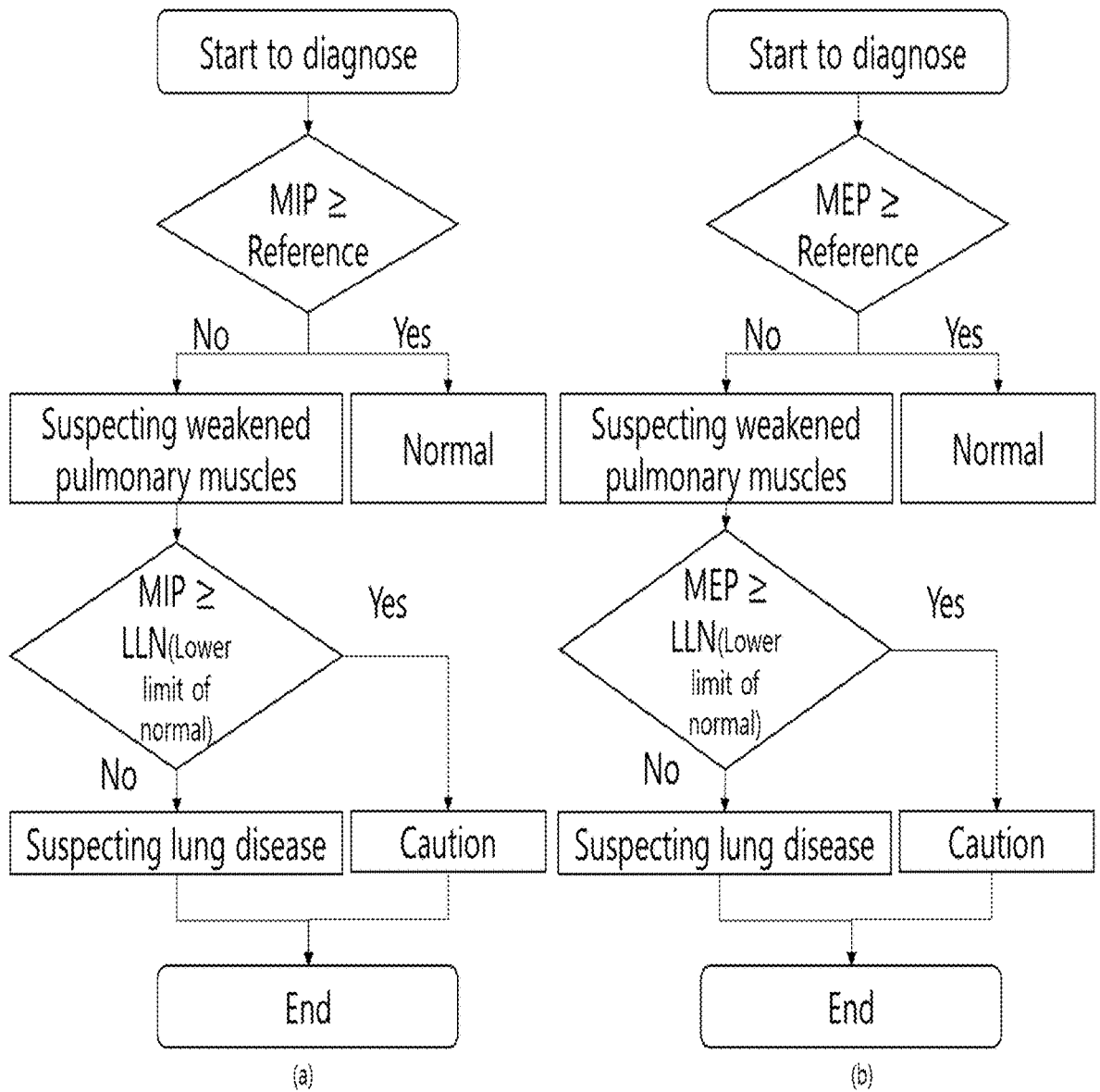
FIG. 12 is a flow chart showing an MIP and MEP diagnostic process of the portable breathing measurement and breathing exercise device according to an embodiment of the present invention.

Additionally, referring to FIG. 12, the control unit 400 compares the user's maximum inspiration pressure (MIP) or maximum expiration pressure (MEP) with a reference value to determine whether the MIP or the MEP is above the reference value. In this instance, when the user's MIP or MEP is above the reference, the control unit 400 determines that the user is in a normal state. Conversely, when the user's MIP or MEP is below the reference value, the control unit 400 generates a warning signal suspecting weakened pulmonary muscles. In addition, when the user's MIP or MEP is below the reference value, the control unit 400 determines whether the user's MIP or MEP falls below the preset minimum lower limit of normal (LLN). In this instance, when the user's MIP or MEP is above the preset minimum lower limit of normal (LLN), the control unit 400 generates a caution signal. Moreover, when the user's MIP or MEP falls below the preset minimum lower limit of normal (LLN), the control unit 400 generates a warning signal suspecting a lung disease. Such warning signals are saved or output respectively to the personal web program 401, the administrator web program 402, the personal display 501, the administrator display 502, and the application 510.

Figure 13:
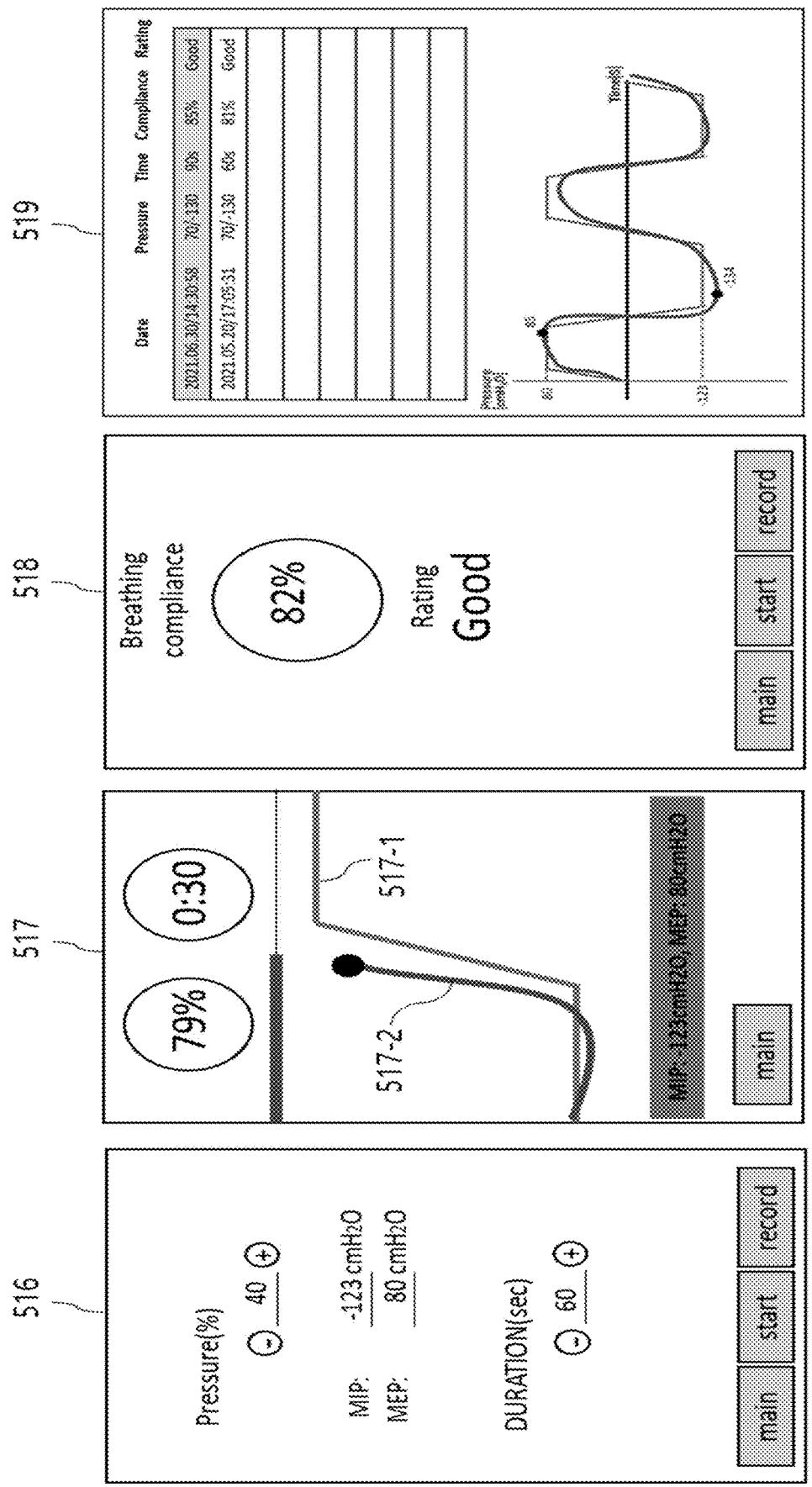
FIG. 13 is a view illustrating a screen of a display part or an application of the portable breathing measurement and breathing exercise device according to an embodiment of the present invention.

In addition, referring to FIG. 13, (a), the breathing exercise control window 516 includes a button to allow adjustment of level by 1 cm H2O or 1% and a button to adjust the measurement time at 10-second intervals, wherein the level is set to average values according to gender and age by default, and the measurement time is set to one minute by default. Additionally, the pressure ranges from 10% to 100% and can be adjusted by 5%. Accordingly, the MIP and MEP values are automatically changed and displayed. In this instance, the time can also be adjustable by 30 seconds. The default setting for the pressure may be 40% of the MIP and MEP values according to gender and age.

Furthermore, referring to FIG. 13, (b), the personal display 501 displays the optimized respiratory guideline 517-1 determined by the user's gender and age, with both maximum and minimum values, and displays the user's actual respiratory line 517-2 in real-time, thereby allowing the user to conduct breathing exercises by comparing the respiratory guideline 517-1 and the user's actual respiratory line 517-2. Moreover, the personal display 501 may display the match rate between the respiratory guideline 517-1 and the respiratory line 517-2 and display the duration of breathing exercise by comparing the respiratory guideline 517-1 and the user's actual respiratory line 517-2. In this instance, the exhalation duration may be five seconds, and the inhalation duration may be three seconds. Additionally, referring to FIG. 13, (c), the results of the breathing exercise, ratings according to match rate, and respiratory muscle age can be displayed. In addition, referring to FIG. 13, (d), a daily breathing exercise result window 519 may be displayed.

Each of the personal display 501 and the administrator display 502 may include an application 510 which receives and stores measurement values from the sensor unit 300 in real-time, analyzes the user's breath based on the measurement values of the sensor unit 300, and supports breathing exercise. The sensor units 300 are provided in plural, and are respectively linked to the personal web program 401, the administrator web program 402, and the application 510. Moreover, each of the personal web program 401, the administrator web program 402, and the application 510 stores information data of at least one reference sensor unit 300 and corrects the measurement values of the sensor units 300 according to the state of the load adjusting part 250 corresponding to each of the plurality of sensor units 300, thereby minimizing a measurement error between the different sensor units 300. Here, the information data of the reference sensor unit 300 refers to the property values of a standard pressure sensor set among various types of pressure sensors. That is, the plurality of sensor units 300 may be different models with different methods or components for measuring pressure, and are to correct errors between measurement values. Furthermore, the state of the load adjusting part 250 may pertain to whether the adjustment hole 253 is opened or not. For example, the portable breathing measurement and breathing exercise device of the invention may include different types of the mouthpiece parts 200 or different types of sensor units 300. Accordingly, even if the same user performs breathing measurement, there may be different measurement values. Therefore, in order to solve the problem, the property values of the standard sensor unit 300 are stored in the personal web program 401, the administrator web program 402, and the application 510. Upon linkage, the property values of the plurality of sensor units 300 are respectively stored in the personal web program 401, the administrator web program 402, and the application 510. Based on the above, the personal web program 401, the administrator web program 402, and the application 510 compare the property values of the standard sensor unit 300 with those of the different sensor units 300 to correct the measurement values, thereby minimizing measurement errors. Additionally, one portable breathing measurement and breathing exercise device may include the plurality of sensor units 300.

As a result, the application 510 allows the user to continue breathing exercises and measurements without being bored, and can encourage children's interest and participation in breathing exercises and measurements.

Next, the portable breathing measurement and breathing exercise device may further include a pressure unit 600 which is detachably provided between the inlet 210 and the mouthpiece body 220. That is, one end of the pressure unit 600 is inserted into the inlet 210, and the other end of the pressure unit 600 is inserted into the mouthpiece body 220, such that the pressure unit 600 is coupled between the inlet 210 and the mouthpiece body 220. In this instance, rings (not illustrated) which is inserted into grooves (not illustrated) formed on the inlet 210 and the mouthpiece body 220 may be provided at both ends of the pressure unit 600, and the pressure unit 600 can be formed in any shape as long as it is detachable between the inlet 210 and mouthpiece body 220.

Here, the pressure unit 600 serves to adjust the flow load of the user's inhalation or exhalation passing through the inlet 210. That is, the pressure unit 600 controls the amount of air flowing into the mouthpiece body 220 during the user's inhalation or exhalation. In other words, it means that when the pressure unit 600 is provided, the amount of air flowing into the mouthpiece body 220 due to the user's inhalation or exhalation is reduced compared to when the pressure unit 600 is not provided.

In this instance, the pressure unit 600 allows air to flow when the inhalation or the exhalation is performed with a pressure exceeding a preset pressure value, and blocks the flow of air when the inhalation or the exhalation is performed with a pressure below the preset pressure value.

Figure 14:
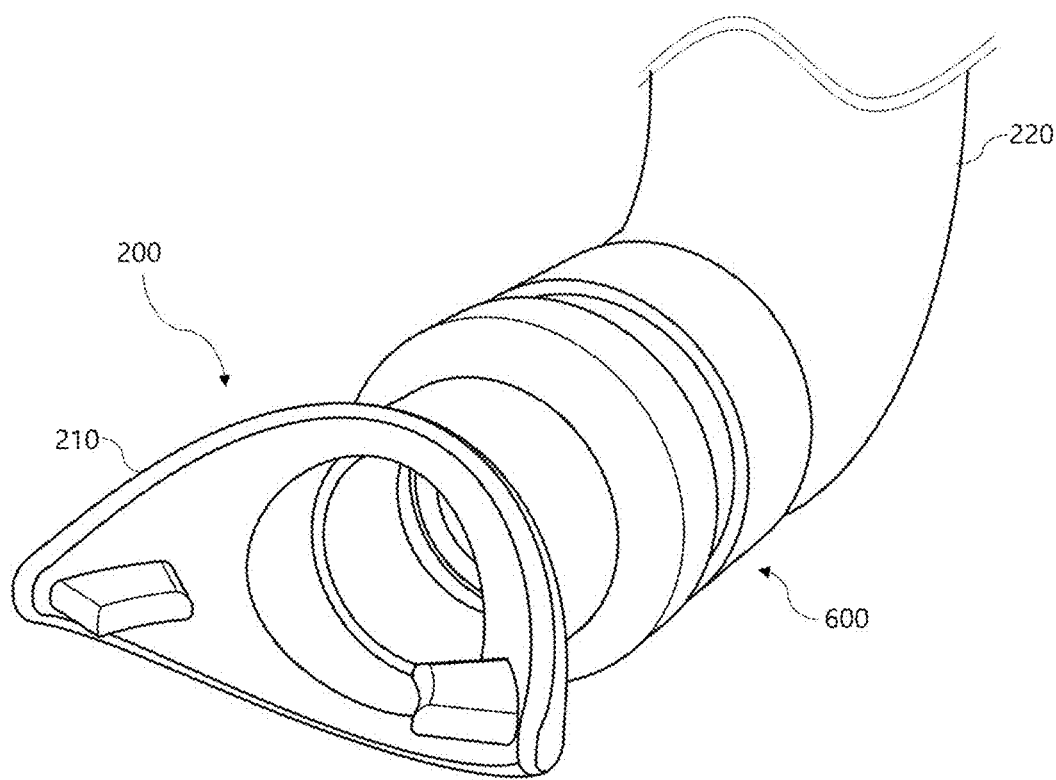
FIG. 14 is an enlarged view illustrating the mouthpiece part and a pressure unit of the portable breathing measurement and breathing exercise device according to an embodiment of the present invention.
Figure 15:
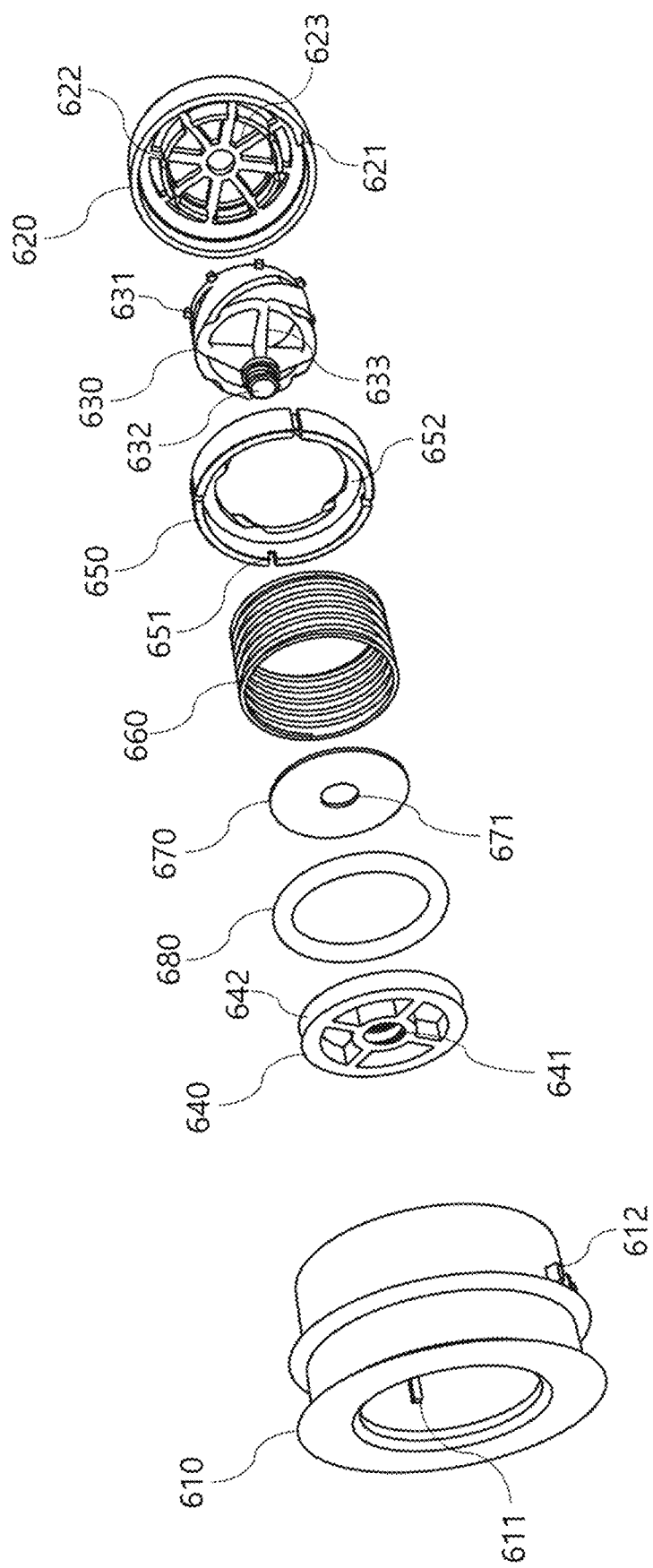
FIG. 15 is a view illustrating the pressure unit of the portable breathing measurement and breathing exercise device according to an embodiment of the present invention.

In more detail, referring to FIGS. 14 and 15, the pressure unit 600 includes: a cylindrical frame part 610 having an empty space formed inside, an adjustment cover 620 provided in a manner that wraps around one end side of the frame part 610, a main filler 630 provided inside the frame part 610 and coupled to the inner surface of the adjustment cover 620, a sub-filler 640 coupled to the end of the main filler 630, a regulator 650 having a hollow formed inside into which the main filler 630 is inserted such that the regulator 630 is coupled with the main filler 630, a spring 660 having one end interfered with the regulator 650 and the other end interfered with the sub-filler 640, a barrier 670 pivotally coupled to one end side of the main filler 630 and provided parallel to the sub-filler 640, and a sealing member 680 provided between the sub-filler 640 and the frame part 610.

Figure 16:
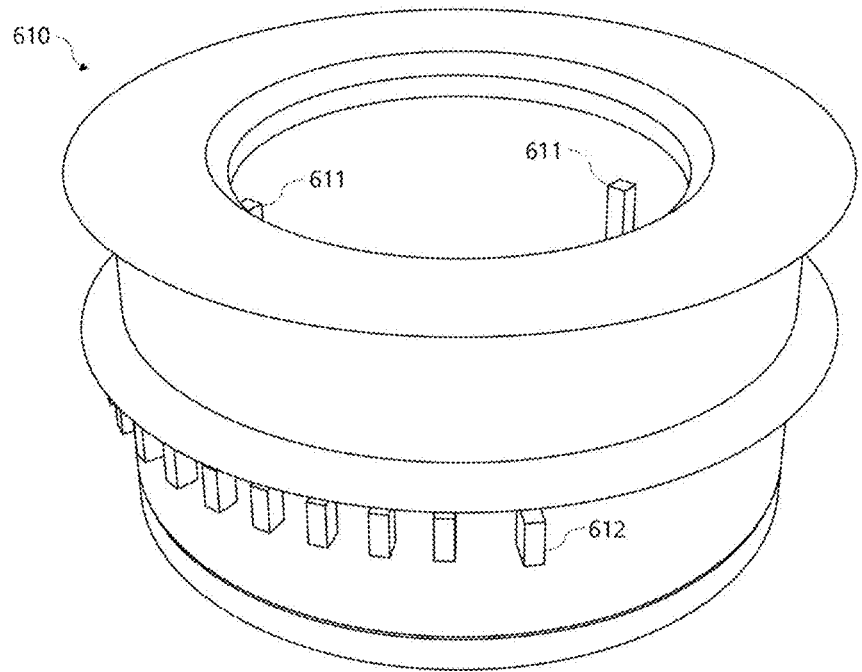
FIG. 16 is a view illustrating a frame part of the portable breathing measurement and breathing exercise device according to an embodiment of the present invention.

Referring to FIG. 16, the frame part 610 has a 'C'-shaped cross-section with a hollow formed inside, and the sub-filler 640 is inserted into the hollow. Additionally, the frame part 610 is inserted and fixed into the mouthpiece body 220, and prevents foreign substances from infiltrating inside.

Here, the frame part 610 includes: rail parts 611 which protrude from the inner circumferential surface of the frame part 610 to guide the linear movement of the regulator 650; and a plurality of adjustment protrusions 612 provided to protrude from the outer circumferential surface of the frame part 610. For example, the rail parts 611 respectively couple with rail grooves 651 to guide the linear movement of the regulator 650 in response to the user's inhalation and exhalation. Moreover, the plurality of adjustment protrusions 612 can be radially arranged at regular intervals along the outer circumferential surface of the frame part 610. In this instance, the plurality of protrusions 612 interfere with an elastic protrusion 621, which will be described later, thereby selectively fixing the adjustment cover 620.

Figure 17:
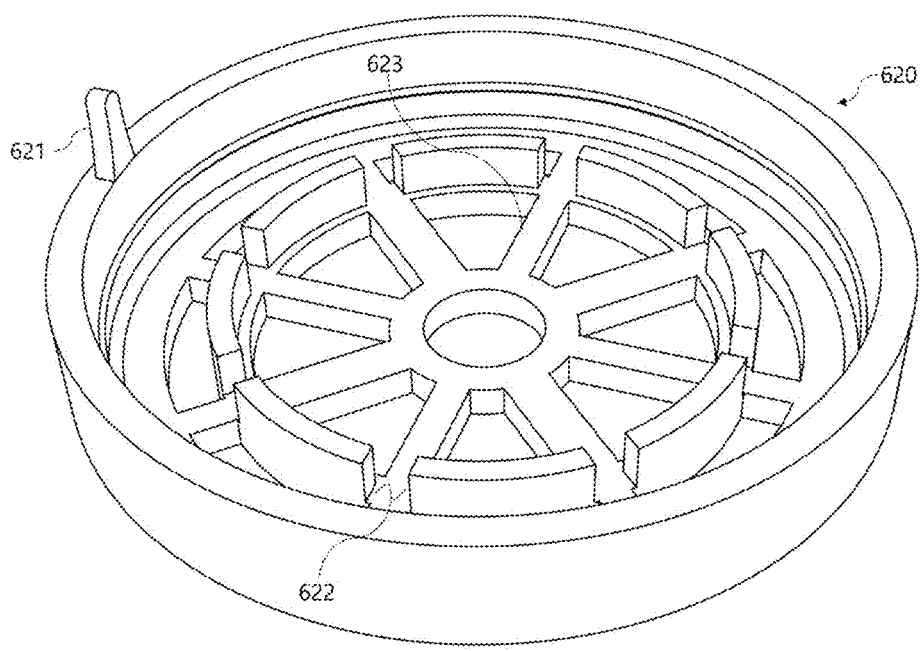
FIG. 17 is a view illustrating an adjustment cover of the portable breathing measurement and breathing exercise device according to an embodiment of the present invention.

Referring to FIG. 17, the adjustment cover 620 has a 'C'-shaped cross-section and is provided to wrap around one end side of the frame part 610. In this instance, the inner circumferential surface of the adjustment cover 620 may have a spiral groove (not illustrated) or a spiral protrusion (not illustrated). That is, the adjustment cover 620 can couple with the spiral protrusion (not illustrated) or the spiral groove (not illustrated) formed on the outer circumferential surface of one side of the frame part 610 while rotating in contact with the spiral protrusion or the spiral groove.

Here, the adjustment cover 620 includes an elastic protrusion 621 which protrudes from an end of the adjustment cover 620. For example, the elastic protrusion 621 is formed to protrude from the outer circumferential surface of the adjustment cover 620 in the direction of the adjustment protrusions 612. Therefore, the elastic protrusion 621 is placed between the adjustment protrusions 612 to fix the adjustment cover 620. When the adjustment cover 620 is rotated to fix the adjustment cover 620 to the frame part 610, the elastic protrusion 621 is bent in the upward direction of the plurality of adjustment protrusions 612 by elasticity of the elastic protrusion. That is, the elastic protrusion 621 is formed of a deformable elastic material.

Moreover, the adjustment cover 620 includes a plurality of fitting slots 622 arranged radially to fix the main filler 630. In this instance, fitting protrusions 631, which will be described later, are inserted into the plurality of fitting slots 622, thereby fixing the adjustment cover 620 to the main filler 630. The plurality of fitting slots 622 are longitudinally elongated to prevent the fitting protrusions 631 from being separated from the fitting slots 622 even when the main filler 630 is moved linearly.

Moreover, the adjustment cover 620 includes a plurality of cover ribs 623 arranged radially around the center of the adjustment cover 620 to allow the flow of the user's inhalation or exhalation. That is, the cover ribs 623 are configured to form an empty space on the outer circumferential surface of the adjustment cover 620 to ensure the rigidity of the adjustment cover 620 and to allow the flow of the user's inhalation or exhalation.

Figure 18:
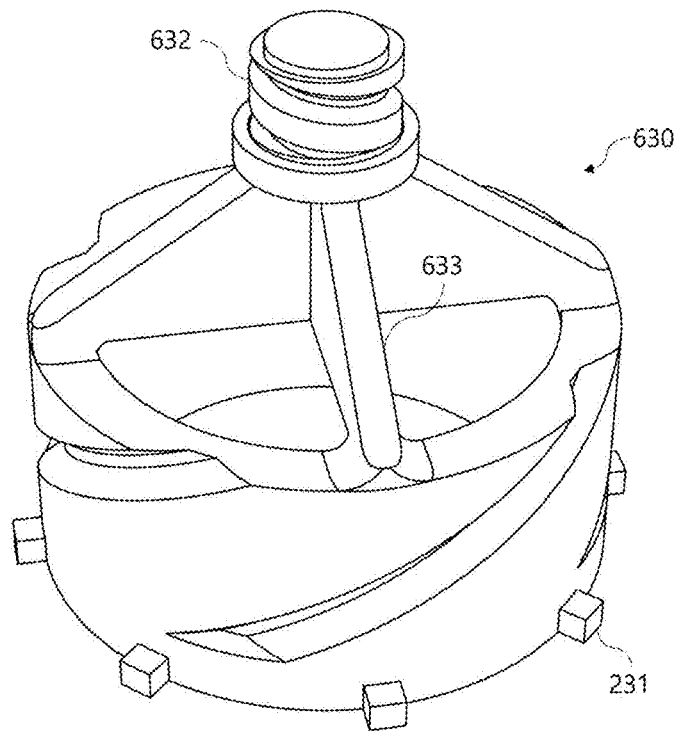
FIG. 18 is a view illustrating a main filler of the portable breathing measurement and breathing exercise device according to an embodiment of the present invention.

Referring to FIG. 18, the main filler 630 is inserted into the frame part 610 and coupled to the adjustment cover 620. In this instance, the main filler 630 includes a plurality of fitting protrusions 631 protruding from the outer circumferential surface of the main filler 630 and arranged radially. The plurality of fitting protrusions 631 have the shape corresponding to the plurality of fitting slots 622, and are inserted into the fitting slots 622, so that the main filler 630 is coupled to the adjustment cover 620. Here, the main filler 630 moves linearly in a direction of contracting the spring 660 during the user's inhalation and moves in a direction of expanding the spring 660 during the user's exhalation.

Additionally, the main filler 630 also includes a shaft 632 which is inserted into the through-hole 641 and rotationally coupled to a spiral thread formed on the inner circumferential surface of the through-hole 641. The shaft 632 protrudes towards the sub-filler 640 from the center of the main filler 630. In this instance, a spiral thread may be formed on the outer circumferential surface of the shaft 632 allowing for rotational coupling with the through-hole 641.

Additionally, the main filler 630 includes a plurality of main filler ribs 633 arranged radially around the center of the main filler 630 to allow the flow of the user's inhalation or exhalation. The plurality of main filler ribs 633 are configured to form an empty space in the main filler 630 to ensure the rigidity of the main filler 630 and to allow the flow of the user's inhalation or exhalation.

Moreover, the plurality of main filler ribs 633 are gradually inclined to gather towards the center of the shaft 632 as they approach the end of the shaft 632. Accordingly, the barrier 670 is bent and comes into contact with the outer circumferential surface of the main filler ribs 633 during the user's exhalation.

Figure 19:
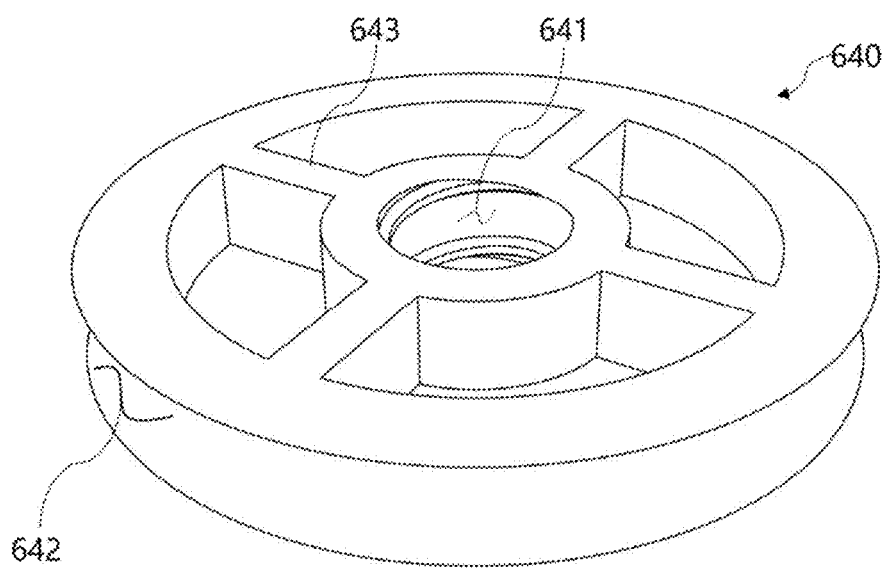
FIG. 19 is a view illustrating a sub-filler of the portable breathing measurement and breathing exercise device according to an embodiment of the present invention.

Referring to FIG. 19, the sub-filler 640 is disc-shaped and moves linearly in the same direction as the main filler 630 during the linear movement of the main filler 630. Furthermore, the sub-filler 640 includes: a through-hole 641 formed through the center of the sub-filler 640; and a sealing groove 642 formed on the outer circumferential surface of the sub-filler 640 to prevent separation of the sealing member 680. In this instance, at least a portion of the sub-filler 640 can be inserted into or drawn out of the hollow of the frame 210 due to the user's inhalation or exhalation.

Moreover, the sub-filler 640 includes a plurality of sub-filler ribs 643 arranged radially around the center of the sub-filler 640 to allow the flow of the user's inhalation or exhalation. The plurality of sub-filler ribs 643 are configured to form an empty space in the sub-filler 640 to ensure the rigidity of the sub-filler 640 and to allow the flow of the user's inhalation or exhalation.

Figure 20:
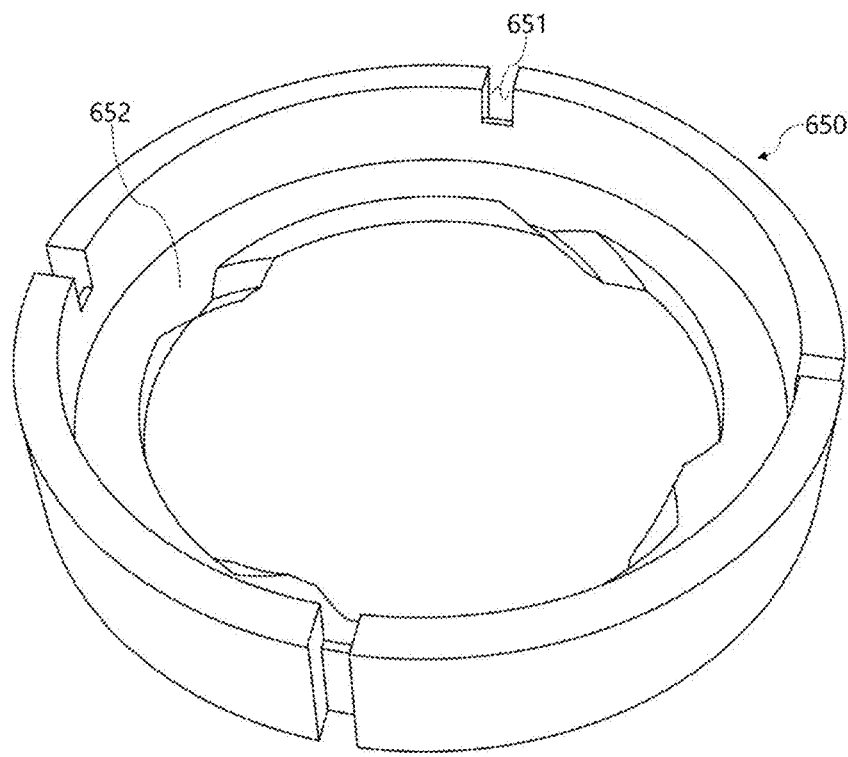
FIG. 20 is a view illustrating a regulator of the portable breathing measurement and breathing exercise device according to an embodiment of the present invention.

Referring to FIG. 20, the regulator 650 has a hollow formed therein, and the hollow of the regulator 650 is formed to correspond to the outer circumferential surface of the main filler 630. That is, the main filler 630 is inserted and fixed into the hollow of the regulator 650. In this instance, the regulator 650 includes a plurality of rail grooves 651 arranged radially along the outer circumferential surface thereof. That is, the rail part 611 is inserted into at least one of the plurality of rail grooves 651 to move linearly in the same direction as the linear movement of the main filler 630.

In addition, the regulator 650 includes an interference part 652 protruding from the inner circumferential surface of the regulator 650 toward the center thereof to accommodate the spring 660.

Figure 21:
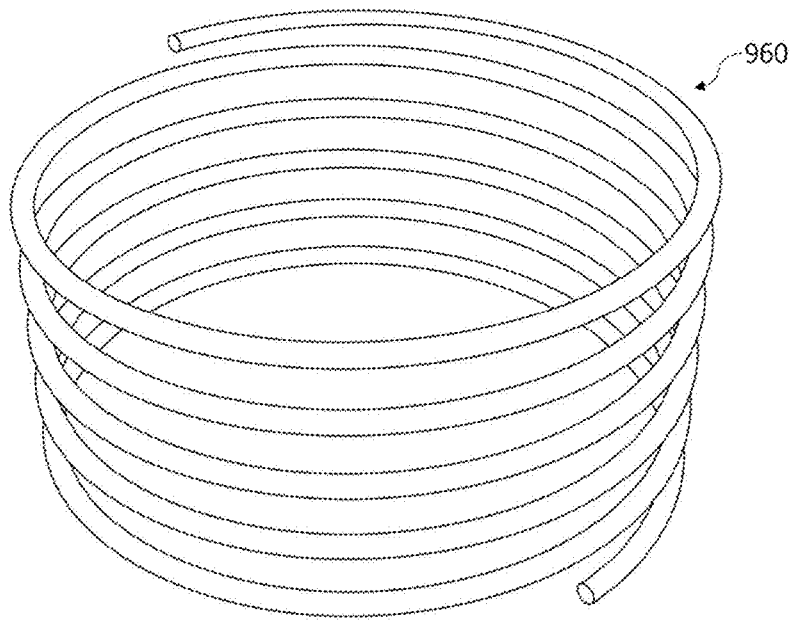
FIG. 21 is a view illustrating a spring of the portable breathing measurement and breathing exercise device according to an embodiment of the present invention.

Referring to FIG. 21, the spring 660 is provided between the sub-filler 640 and the regulator 650. That is, one end of the spring 660 is placed on the interference part 652, and the other end is placed on the side of the sub-filler 640. Here, the spring 660 is compressed while the main filler 630 pushes the regulator 650 in one direction as the adjustment cover 620 is coupled to the frame part 610.

Figure 22:
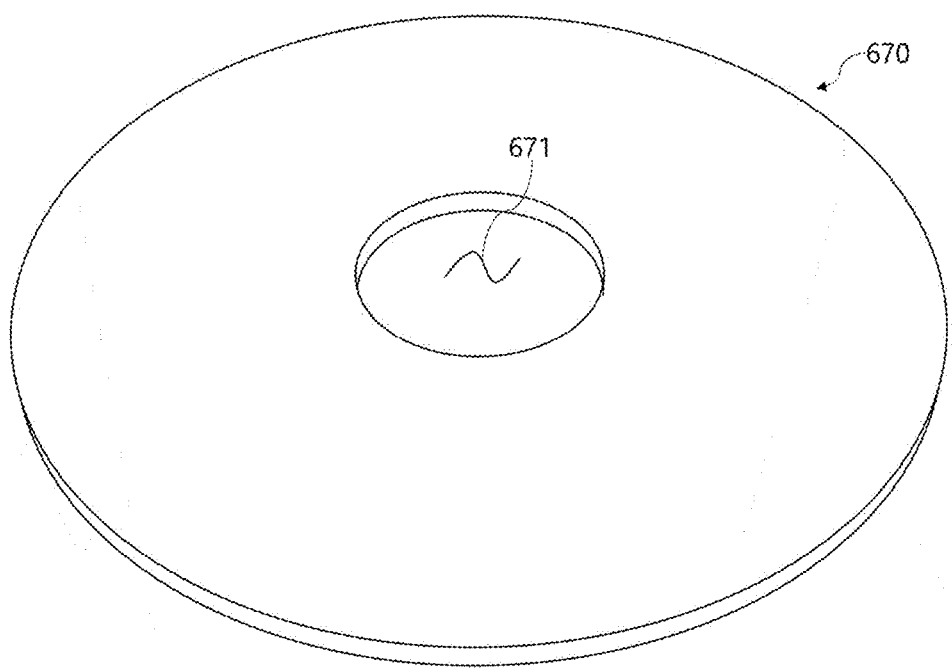
FIG. 22 is a view illustrating a barrier of the portable breathing measurement and breathing exercise device according to an embodiment of the present invention.

Referring to FIG. 22, the barrier 670 is disc-shaped and provided between the sub-filler 640 and regulator 650, and includes an insertion hole 671 formed at the center of the barrier 670. The insertion hole 671 is inserted into the shaft 632 to fix the barrier 670. Furthermore, the barrier 670 is provided in a manner that covers at least a portion of the sub-filler 640. In other words, the barrier 670 serves to block the empty space between the sub-filler ribs 643. In this instance, the barrier 670 can be formed from a thin, elastic plate material. Therefore, the barrier 670 is bent during the user's exhalation and returns to its original shape after the exhalation. The barrier 670 induces the user to exhale with a force stronger than the elastic force of the barrier 670, thereby enabling the user to perform exhalation exercise during breathing training. Here, the barrier 670 is bent in a direction adjacent to the outer circumferential surface of the main filler ribs 633 during the user's exhalation. The barrier 670 can be made, for example, of silicone material.

Figure 23:
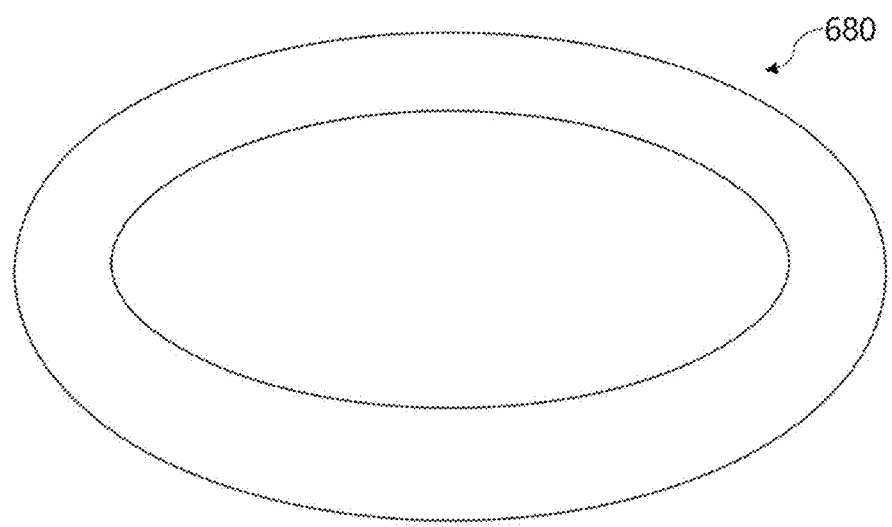
FIG. 23 is a view illustrating a sealing member of the portable breathing measurement and breathing exercise device according to an embodiment of the present invention.

Referring to FIG. 23, the sealing member 680 is made of rubber material and serves to block a gap between the sub-filler 640 and the frame part 610. In this instance, the sealing member 680 is provided along the outer circumferential surface of the sub-filler 640. That is, the sealing member 680 is provided in a state of being placed in the sealing groove 642.

Figure 24:
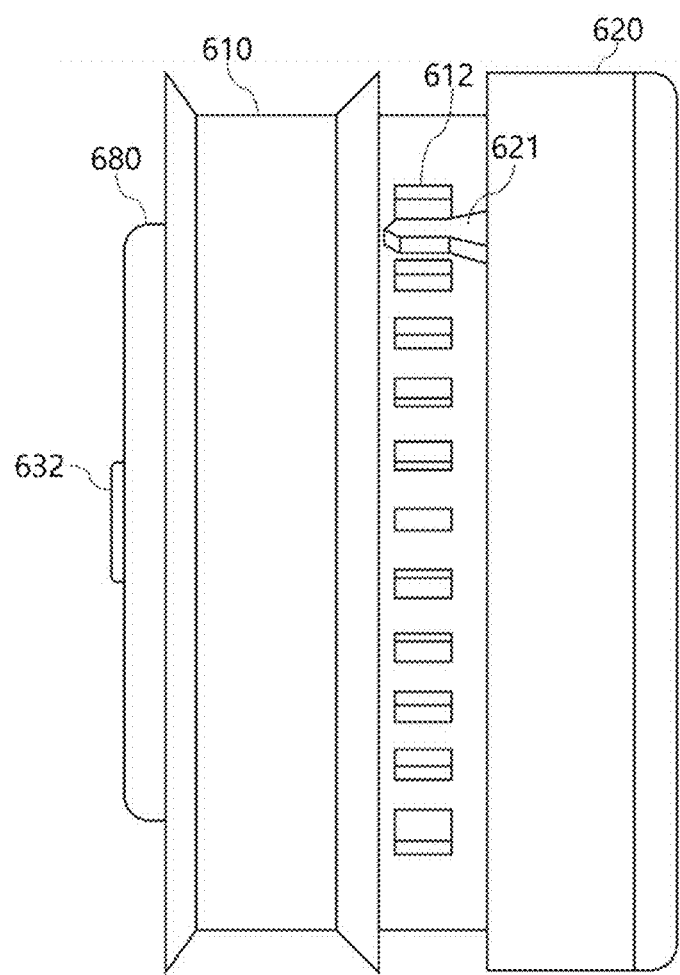
FIG. 24 is a side view illustrating a pressure unit of the portable breathing measurement and breathing exercise device according to an embodiment of the present invention.

Referring to FIG. 24, the compressed state of the spring 660 can be adjusted according to the distance between the adjustment cover 620 and the frame part 610. In other words, when the adjustment cover 620 is coupled to the frame part 610, the distance between the adjustment cover 620 and the frame part 610 is adjusted according to the rotational turns of the adjustment cover 620, thereby adjusting the compression degree of the spring 660. For instance, when the adjustment cover 620 is rotated in one direction in the state in which the adjustment cover 620 is coupled to the frame part 610, the adjustment cover 620 pushes the main filler 630 in the direction of the frame part 610 such that the main filler 630 moves linearly. When the main filler 630 moves linearly toward the frame part 610, the regulator 650 is also moved in the same direction. Accordingly, the spring 660 is compressed. That is, the user's inhalation becomes easier, so the volume of breathing exercise is reduced. Conversely, when the adjustment cover 620 is rotated in the opposite direction in the state in which the adjustment cover 620 is coupled to the frame part 610, the adjustment cover 620 pulls the main filler 630 in the opposite direction of the frame part 610, so the main filler 630 moves linearly. When the main filler 630 moves linearly in the opposite direction to the direction of the frame part 610, the regulator 650 is also moved in the same direction. Accordingly, the spring 660 is expanded. That is, the user's exhalation becomes harder, so the volume of breathing exercise is increased. Consequently, the rotation of the adjustment cover 620 can change the state of the spring 660, thereby regulating the user's breathing intensity.

Figure 25:
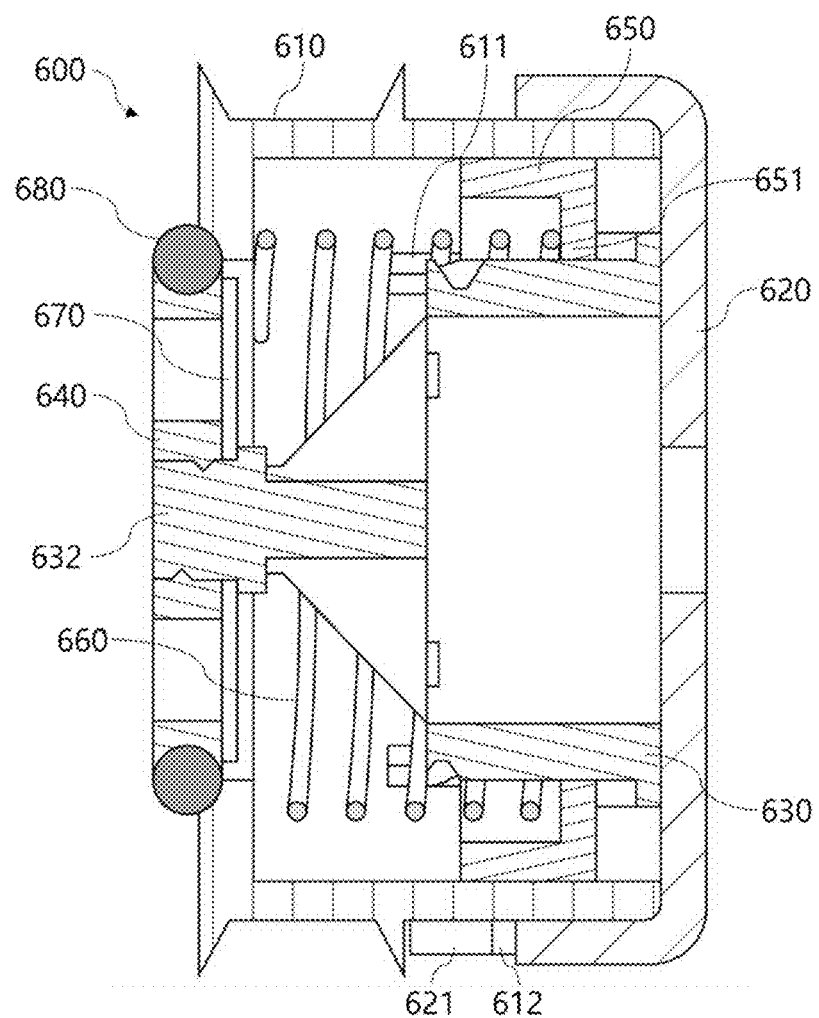
FIG. 25 is a sectional view illustrating the pressure unit of the portable breathing measurement and breathing exercise device according to an embodiment of the present invention.
Figure 26:
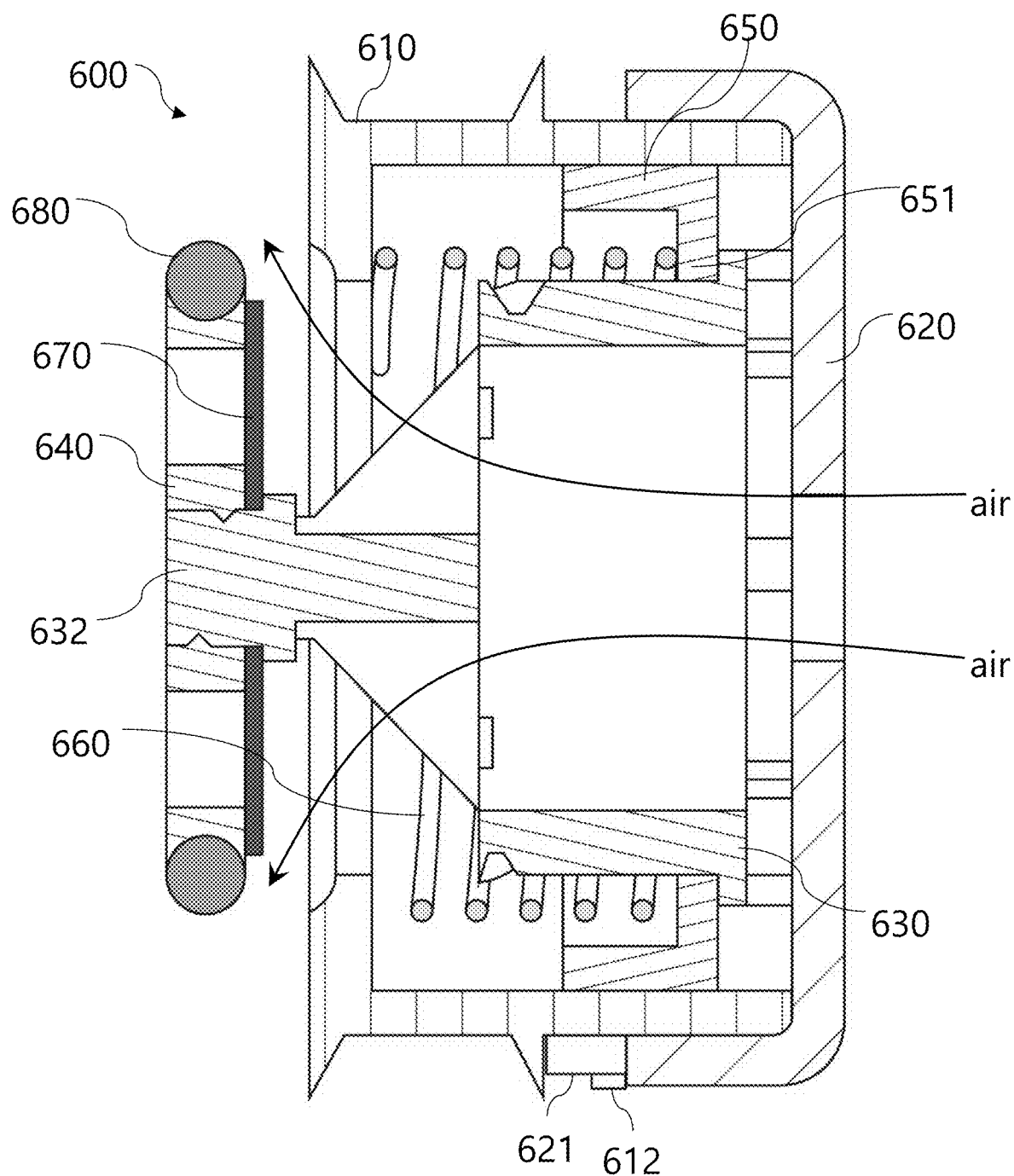
FIG. 26 is a sectional view illustrating the action of the pressure unit during inhalation of the portable breathing measurement and breathing exercise device according to an embodiment of the present invention.
Figure 27:
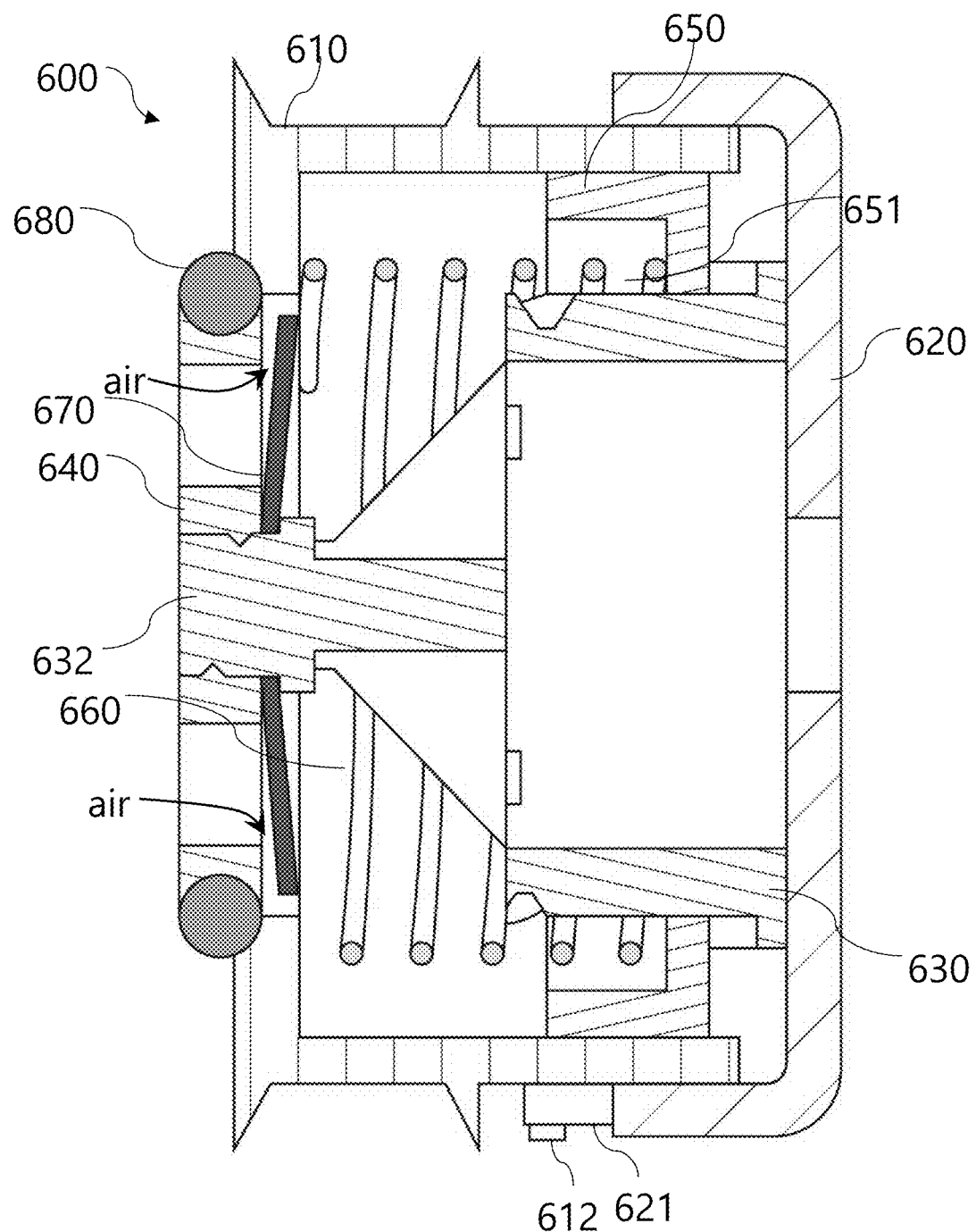
FIG. 27 is a sectional view illustrating the action of the pressure unit during exhalation of the portable breathing measurement and breathing exercise device according to an embodiment of the present invention.

Through such a configuration, referring to FIGS. 25 to 27, the outside air can pass through the pressure unit 600 only when the user inhales with a force stronger than the elastic force of the spring 660, thereby enabling the user to perform inhalation exercise during breathing training.

In more detail, when the user inserts the inlet 210 into the mouth in the state in which the pressure unit 600 is coupled to the mouthpiece body 220, the flow of air is regulated by the pressure unit 600. First, during the user's inhalation, the outside air flows in, and then, is stopped by the barrier 670. In this instance, when the user inhales with a pressure exceeding the elastic force of the spring 660, the sub-filler 640 is drawn out of the hollow of the frame part 610, and a flow path is formed between the sub-filler 640 and the frame part 610. That is, only when the user inhales with a pressure that exceeds the elastic force of the spring 660, at least a portion of the sub-filler 640 is drawn out of the hollow of the frame part 610 to form a flow path, such that outside air can flow inside. Thereafter, when the user stops inhalation, the sub-filler 640 is inserted into the hollow of the frame part 610 by the elasticity of the spring 660 to return to its original position.

Referring to FIG. 22, during the user's exhalation, the inside air flows, and then, is stopped by the barrier 670. In this instance, when the user exhales with pressure exceeding the elastic force of the barrier 670, the barrier 670 is bent to form a flow path between the barrier 670 and the sub-filler 640. That is, only when exhalation is performed with pressure exceeding the elastic force of the barrier 670, the barrier 670 is bent toward the main filler 630, and at least a portion of the sub-filler 640 is opened to form a flow path, such that the inside air can flow to the outside.

TABLE 1

| Male | Twenties | Thirties | Forties | Fifties | Sixties |
|---|---|---|---|---|---|
| MIP (cmH$_2$O) | 111.8 | 107.7 | 103.6 | 99.5 | 95.4 |
| 30% MIP | 33.54 | 32.31 | 31.08 | 29.85 | 28.62 |

TABLE 2

| Female | Twenties | Thirties | Forties | Fifties | Sixties |
|---|---|---|---|---|---|
| MIP (cmH$_2$O) | 95.8 | 89.7 | 83.6 | 77.5 | 71.4 |
| 30% MIP | 28.74 | 26.91 | 25.08 | 23.25 | 21.42 |

TABLE 3

|  | Runner | Swimmer |
|---|---|---|
| MIP (cmH$_2$O) | 134 | 115 |
| 80% MIP | 107.2 | 92 |

In addition, Table 1 and Table 2 show average respiratory pressure values by age group, and propose appropriate exercise numerical values. For the general population, a pressure value of 30% is appropriate, and for athletes, a pressure value of 80% is appropriate. The spring 660 allows adjustment of pressure values within the range of 20 to 100 cmH2O.

Consequently, breathing exercises can be performed by using the spring 660 and the barrier 670, and the intensity of the exercises can be adjusted by replacing the spring 660 and the barrier 670. Furthermore, the user can focus on any one of the inhalation and exhalation exercises when any one of the spring 660 and the barrier 670 is coupled. For example, when the barrier 670 is not coupled to the pressure unit 600 but only the spring 660 is coupled to the pressure unit 600, the user can focus on inhalation exercises. Conversely, when the spring 660 is not coupled to the pressure unit 600 but only the barrier 670 is coupled to the pressure unit 600, the user can focus on exhalation exercises.

Figure 28:
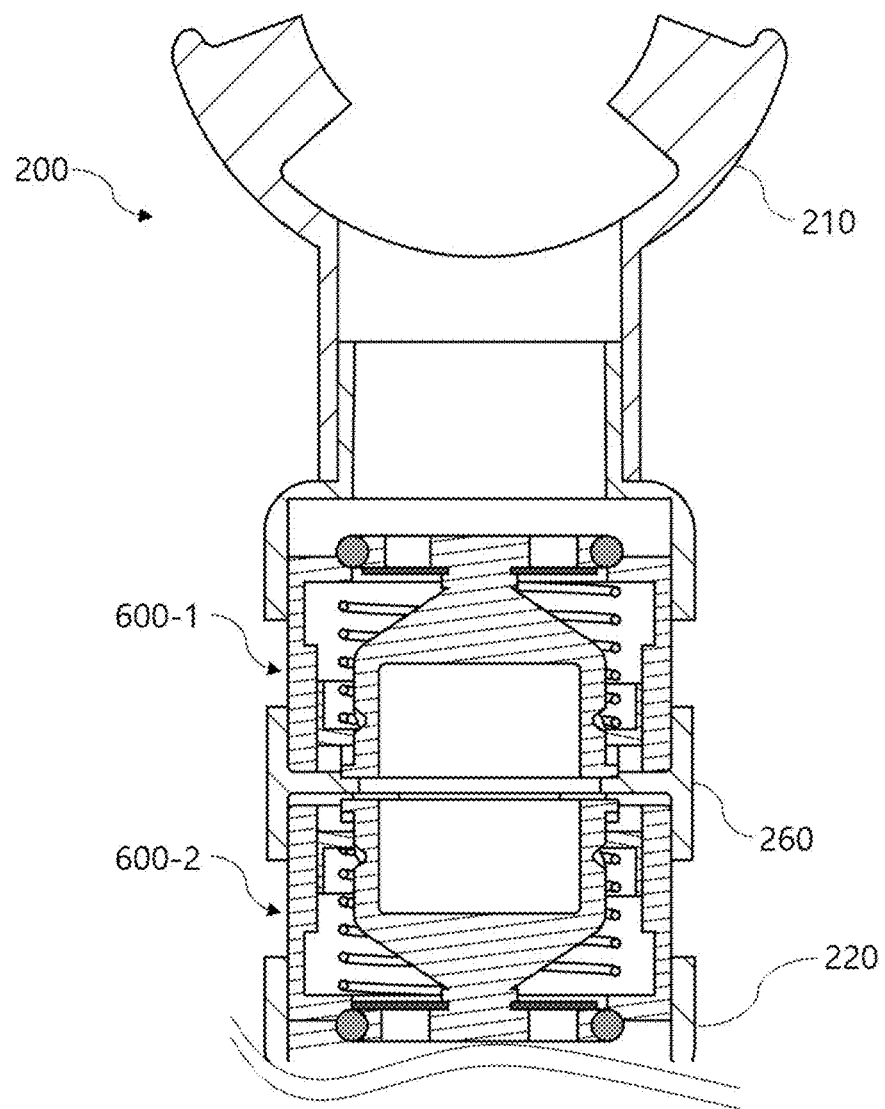
FIG. 28 is a view illustrating two pressure units of the portable breathing measurement and breathing exercise device according to another embodiment of the present invention.

Next, referring to FIG. 28, the mouthpiece part 200 may further include a pressure unit connector 260 which at least partially surrounds around the outer circumferential surface of the pressure unit 600. That is, one end of the pressure unit connector 260 is coupled with a first pressure unit 600-1, and the other end is coupled with a second pressure unit 600-2. Here, two pressure units 600 are coupled with the mouthpiece part 200 in opposing directions. That is, the two pressure units 600 are provided to be in line symmetry about the central axis in the length direction of the pressure unit connector 260. In this instance, the pressure unit connector 260 is rotatably coupled, such that the adjustment cover 620 can adjust pressure by rotation of the pressure unit cap 260 when the pressure unit cap 260 rotates. Consequently, the mouthpiece part 200 and the two pressure units 600 are coupled for easy carrying, thereby allowing the user to perform exhalation and inhalation exercises.

Those skilled in the art will understand that the present invention can be implemented as other concrete forms without changing the inventive concept or essential features.

Therefore, these embodiments as described above are only proposed for illustrative purposes and do not limit the present invention. It will be apparent to those skilled in the art that a variety of modifications and variations may be made without departing the spirit and scope of the present invention as defined by the appended claims. Further, such modifications and variations should not be understood independently from the technical idea or perspective of the present invention.

EXPLANATION OF REFERENCE NUMERAL

100: main body
101: left case
102: right case
103: cap
104: board
110: cylindrical part
111: guide part
120: slit part
120-1: first slit part
120-2: second slit part
120-3: third slit part
120-4: fourth slit part
130: main hole
140: sub-hole
150: display part
161: power switch
162: operation switch
170: charging terminal
200: mouthpiece part
210: inlet
220: mouthpiece body
230: filter part
240: flexible part
250: load adjusting part
251: coupling part
252: protrusion
253: adjustment hole
253-1: first adjustment hole
253-1: second adjustment hole
253-3: third adjustment hole
253-4: fourth adjustment hole
260: connector
300: sensor unit
400: control unit
401: personal web program
402: administrator web program
500: display unit
501: personal display
502: administrator display
510: application
511: recent record window
512: detailed measurement result window
513: summary result window
514: result graph window
515: correction setting window
516: breathing exercise control window
517: real-time breathing exercise result window
517-1: respiratory guideline
517-2 user respiratory line
518: final breathing exercise result window
519: daily breathing exercise result window
600: pressure unit
610: frame part
611: rail part
612: adjustment protrusion
620: adjustment cover
621: elastic protrusion
622: fitting slot
623: cover rib
630: main filler
631: fitting protrusion
632: shaft
633: main filler rib
640: sub-filler
641: through-hole
642: sealing groove
643: sub-filler rib
650: regulator
651: rail groove
652: interference part
660: spring
670: barrier
671: insertion hole
680: sealing member

The invention claimed is:

1. A portable breathing measurement and exercise device comprises:
a main body;
a mouthpiece assembly which is coupled to one side of the main body;
a sensor module provided inside the main body and configured to measure a pressure of a user's breath through the mouthpiece assembly;
a controller configured to receive measurement values from the sensor module, store the measurement values in real-time, analyze the user's breath based on the measurement values, and provide an exercise schedule; and
a display device configured to output analysis results and the exercise schedule from the controller,
wherein the mouthpiece assembly includes a load regulator configured to control a flow of air moving in and out of the mouthpiece assembly and the main body part response to the user's breath,
wherein the controller includes:
a personal web program configured to receive and store the measurement values from the sensor module in real-time;
a web server linked to the personal web program and configured to receive and store the measurement values from the sensor module in real-time; and
an administrator web program linked to the web server and configured to receive and store the measurement values from the sensor module in real-time,
wherein the display device includes:
a personal display configured to output the measurement values of the sensor module; and
an administrator display located remotely from the personal display and configured to output the measurement values of the sensor module, thereby allowing an administrator to monitor the measurement values of the sensor module remotely,
wherein if the measurement values of the sensor module fall below a preset threshold or are not transmitted for a preset duration, the controller sends an alarm signal to the administrator web program and controls an output of the alarm signal to the administrator display.

2. The portable breathing measurement and exercise device according to claim 1, wherein the mouthpiece assembly includes:
an inlet configured to be inserted into the user's mouth;
a mouthpiece body provided at a bottom of the inlet and formed in a cylindrical shape;
a filter provided inside the mouthpiece body; and
a flexible extension which extends from a bottom of the mouthpiece body,
wherein the load regulator is provided at a lower portion of the flexible extension and is coupled to an upper portion of the main body.

3. The portable breathing measurement and exercise device according to claim 2, wherein the main body includes:
- a cylindrical piece which protrudes upwards from a top portion of the main body and has an empty space formed inside;
- a plurality of slits provided along a lower outer circumference of the cylindrical piece and
- a main hole formed at least partially through the cylindrical piece, wherein the load regulator includes:
- a coupling sleeve configured to surround an outer circumference of the cylindrical piece
- a protrusion formed at an end of the coupling sleeve and shaped to correspond to a shape of the plurality of slits; and
- an adjustment hole formed at least partially through the coupling sleeve, such that the main body and the load regulator are coupled with each other when the protrusion is inserted into any one of the plurality of slit parts slits.

4. The portable breathing measurement and exercise device according to claim 1, wherein each of the personal display and the administrator display includes:
- an application which receives and stores measurement values from the sensor module in real-time, analyzes the user's breath based on the measurement values of the sensor module, and supports breathing exercise, wherein a plurality of sensor modules including the sensor module are provided, and are respectively linked to the personal web program, the administrator web program, and the application, and wherein each of the personal web program, the administrator web program, and the application stores information data of at least one reference sensor module, and corrects measurement values of the plurality of sensor modules according to a state of the load regulator corresponding to each of the plurality of sensor modules, thereby minimizing a measurement error between different sensor modules.

* * * * *